(12) United States Patent
North

(10) Patent No.: US 9,006,425 B2
(45) Date of Patent: Apr. 14, 2015

(54) ALUMINUM COMPLEXES AND THEIR USE IN THE SYNTHESIS OF CYCLIC CARBONATES

(75) Inventor: Michael North, Newcastle Upon Tyne (GB)

(73) Assignee: University of York, York (GB)

(*) Notice: Subject to any disclaimer, the term of this patent is extended or adjusted under 35 U.S.C. 154(b) by 754 days.

(21) Appl. No.: 13/254,143

(22) PCT Filed: Mar. 17, 2010

(86) PCT No.: PCT/GB2010/000488
§ 371 (c)(1), (2), (4) Date: Sep. 8, 2011

(87) PCT Pub. No.: WO2010/106324
PCT Pub. Date: Sep. 23, 2010

(65) Prior Publication Data
US 2011/0319634 A1 Dec. 29, 2011

(30) Foreign Application Priority Data
Mar. 18, 2009 (GB) .................................. 0904654.1

(51) Int. Cl.
*C07F 5/06* (2006.01)

(52) U.S. Cl.
CPC ...................................... *C07F 5/069* (2013.01)

(58) Field of Classification Search
None
See application file for complete search history.

(56) References Cited

U.S. PATENT DOCUMENTS

| | | | |
|---|---|---|---|
| 6,521,561 B1 | 2/2003 | Jacobsen et al. | |
| 2008/0214386 A1 | 9/2008 | Takahashi et al. | |
| 2013/0317237 A1* | 11/2013 | North ............................ | 549/230 |

FOREIGN PATENT DOCUMENTS

| | | | |
|---|---|---|---|
| CN | 1789258 | | 6/2006 |
| CN | 1796384 A | | 7/2006 |
| CN | 101020747 A | * | 8/2007 |
| EP | 1 970 199 A1 | | 9/2008 |
| JP | 58222079 A | | 12/1983 |
| JP | 02047134 A | | 2/1990 |
| JP | 2005-202022 A | | 8/1993 |
| JP | 2001 003043 A | | 1/2001 |
| JP | 2001-129397 | | 5/2001 |
| JP | 2005-254068 A | | 9/2005 |
| SK | 0284530 B6 | | 6/2005 |
| WO | 2003 029325 A1 | | 4/2003 |
| WO | 2005 084801 A1 | | 9/2005 |
| WO | 2006 032716 A1 | | 3/2006 |
| WO | 2008/132474 A1 | | 11/2008 |
| WO | WO2008/132474 | | 11/2008 |

OTHER PUBLICATIONS

Melèndez, Jaisiel, et al: "Synthesis of cyclic carbonates from atmospheric pressure carbon dioxide using exceptionally active aluminum (salen) complexes as catalysts" European Journal of Inorganic Chemistry, vol. 2007, No. 21, 2007, pp. 3323-3326, XP00252661, Wiley-VCH Verlag GmbH & Co., KGaA, Weinheim.

Zhang, Xiang, et al.: "Intramolecularly two-centered cooperation catalysis for the synthesis of cyclic carbonates from CO2 and epoxides" Tetrahedron Letters, No. 49 (2008) pp. 6589-6592, Elsevier Ltd.

Sujith S., et al.: "A highly active and recyclable catalytic system for CO2/Propylene Oxide Copolymerization" Agnew Chem. Int. Ed., 2008, vol. 47, pp. 7306-7309, Wiley-VCH Verlag GmbH & Co., KGaA, Weinheim.

Broadwith: "Waste CO2 turned into useful molecules" Chemistry World, Dec. 2009, p. 29, Royal Society of Chemistry, UK.

Clegg, William, et al.: "Cyclic carbonate synthesis catalysed by bimetallic aluminium-salen complexes" Chem. Eur. J., 2010, vol. 16, pp. 6828-6843, Wiley-VCH Verlag GmbH & Co., KGaA, Weinheim.

Clegg, William, et al.: "A Bimetallic Aluminum(salen) complex for the synthesis of 1.3-oxathiolane-2-thiones and 1,3-dithiolane-2-thiones" J. Org. Chem., DOI 10__1021__jo101121h JOC, vol. 75 No. 18, 6201-6207, American Chemical Society, (Aug. 23, 2010).

Melèndez, Jaisiel, et al: "One-component catalysis for cyclic carbonate synthesis" Chem. Commun., 2009, pp. 2577-2579, The Royal Society of Chemistry, UK.

Metcalfe, Ian S., et al.: "An integrated approach to energy and chemicals production" Energy Environ. Sci., 2010, vol. 3, pp. 212-215, The Royal Society of Chemistry, UK.

North, Michael, et al.: "Mechanism of Cyclic Carbonate Synthesis from Epoxides and CO2" Agneew Chem. Int. Ed., 2009, vol. 48, pp. 2946-2948, Wiley-VCH Verlag GmbH & Co., KGaA, Weinheim.

North, Michael, et al.: "A Gas-Phase Flow Reactor for Ethylene Carbonate Synthesis from Waste Carbon Dioxide" Chem. Eur. J., 2009, vol. 15, pp. 11454-11457, Wiley-VCH Verlag GmbH & Co., KGaA, Weinheim.

North, Michael, et al.: "Synthesis of cyclic carbonates from epoxides and CO2" Green Chemistry, 2010, DOI 10, 1039__c0GC00065e, The Royal Society of Chemistry, UK.

North, Michael, et al."Aluminium(salen) and Tetrabutylammonium Bromide CatalysedSynthesis of Cyclic Di- and Trithiocarbonates from Epoxides and Carbon Disulfide" SYNLETT, 2010, No. 4, pp. 0623-0627, Georg Thieme Verlag Stuttgart, New York.

Vanderwal, Christopher D., et al.: "Enantioselective Formal Hydration of a,β-Unsaturated Imides by Al-Catalyzed Conjugate Addition of Oxime Nucleophiles" J.Am. Chem. Soc. 2004, vol. 126, 14724-14725, American Chemical Society.

(Continued)

*Primary Examiner* — Michael Barker
(74) *Attorney, Agent, or Firm* — Steptoe & Johnson LLP

(57) ABSTRACT

Dimeric aluminum catalysts of formula I: and their use in catalyzing the synthesis of cyclic carbonates from epoxides and carbon dioxide.

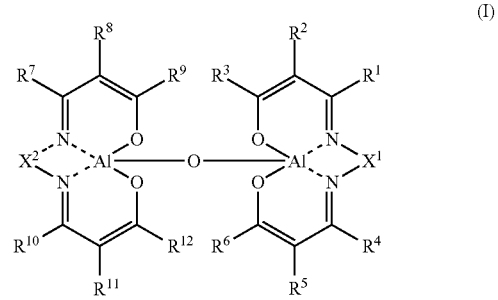

11 Claims, No Drawings

(56) References Cited

OTHER PUBLICATIONS

Larrow, Jay F., et al.: "A Practical Method for the Large-Scale Preparation of [N,N'-Bis(3,5-di-tert-buty Isalicylidene)-1,2-cyclohexanediaminato(2-) ]manganese (III) Chloride, a Highly Enantioselective Epoxidation Catalyst" J. Org. Chem. 1994, vol. 59, 1939-1942, American Chemical Society.

Shen, Yu-Mei, et al.: "Chemical Fixation of Carbon Dioxide Catalyzed by Binaphthyldiamino Zn, Cu, and Co Salen-Type Complexes" J. Org. Chem. 2003, vol. 68, 1559-1562, American Chemical Society.

Wang, Yuhong, et al.: "Five-coordinate organoaluminum acetylides and crystal structure of the hydroxylate, [Salophen(tBu)Al]2O", J. of Organic Chemistry, 2004, vol. 689, 759-765.

Matsumoto, Kazuhiro, et al.: "Catalytic Enantioselective Epoxidation of Unfunctionalized Olefins: Utility of a Ti(Oi-Pr)4-Salan-H2O2 System," Synlett 2006, vol. 20, 3545-3547, Georg Thieme Verlag Stuttgart, New York.

Shitama, Hiroaki, et al.: "Asymmetric epoxidation using aqueous hydrogen peroxide as oxidant: bio-inspired construction of pentacoordinated Mn-salen complexes and their catalysis," Tetrahedron Letters 2006, vol. 47, 3203-3207, Elsevier Ltd.

Gandelman, Mark, et al.: "Highly Enantioselective Catalytic Conjugate Addition of N-Heterocycles to a,β-Unsaturated Ketones and Imides," Chem. Int. Ed. 2005, vol. 44, 2393-2397, Wiley-VCH Verlag GmbH & Co. KGaC, Weinheim.

Kureshy, R.I., et al.: "Environment friendly protocol for enantioselective epoxidation of non-functionalized alkenes catalyzed by recyclable homochiral dimeric Mn(III) salen complexes with hydrogen peroxide and UHP adduct as oxidants," Catalysis Letters, 2006, vol. 107, Nos. 1-2, Springer Science + Business Media, Inc.

Nomura, Nobuyoshi, et al.: "Stereoselective Ring-Opening Polymerization of a Racemic Lactide by Using Achiral Salen- and Homosalen—Aluminum Complexes," Chem Eur. J., 2007, vol. 13, 4433-4451, Wiley-VCH Verlag GmbH & Co. KGaA, Weinheim.

Gurian, Patrick L., et al.: "Aluminium Complexes of N,N,'—Ethylenebis(salicyl ideneimine)-( H2salen). X-Ray Crystal Structures of [{Al(salen)},2(u-O)].MeCN and [Al(OC6H2Me3,-2,4,6)(salen)]," J. Chem. Soc., Dalton Trans. (Inorganic), 1991, vol. 6, 1449-1456.

Atwood, David, et al.: "Group 13 Compounds Incorporating Salen Ligands," Chem. Rev. 2001, vol. 101, 37-52, American Chemical Society.

Gisch, Nicolas, et al.: "Enzymatically Activated cycloSal-d4T-monophosphates: The Third Generation of cycloSal-Pronucleotides," J. Med. Chem. 2007, vol. 50, 1658-1667, American Chemical Society.

Rutherford, Drew, et al.: "Five-Coordinate Aluminum Amides," Organometallics 1996, vol. 15, 4417-4422, American Chemical Society.

Pervaiz, Muhammad, et al.: "Carbon storage potential in natural fiber composites," Resources, Conservation and Recycling 2003, vol. 39, 325-340, Elsevier Science B.V.

Irie, Ryo, et al.: "Enantioselective Expoxidation of Chromene Derivatives using Hydrogen peroxide as a Terminal Oxidant," Synlett 1994, 255-256 (Japan).

Achard, Theirry, R.J., et al.: "Asymmetric Catalysis of Carbon-Carbon Bond-Forming Reactions Using Metal(salen) Complexes," Synlett 2005, No. 12, 1828-1847, Georg Thieme Verlag Stuttgart, New York.

Iida, Takehiko, et al.: "Cyclocondensation of Oxalyl Chloride with 1,2-Glycols," Tetrahedron, 1993, vol. 49, No. 46, 10511-10530, Ferguson Pres, Ltd. UK.

North, Michael, "Synthesis and applications of non-racemic cyanohydrins," Tetrahedron: Asymmetry 2003, vol. 14 147-176, Elsevier Science Ltd.

Dzugan, Sharlene J., et al.: "Factors Affecting Al—C Bond Reactivity of Tetradentate Schiff-Base Organoaluminum Complexes," Inorg. Chem 1986, vol. 25, 2858-2864, American Chemical Society.

Sammis, Glenn M., et al.: "Highly Enantioselective, Catalytic Conjugate Addition of Cyanide to a,β-Unsaturated Imides," J. Am. Chem. Soc. 2003, vol. 125, 4442-4443, American Chemical Society.

Taylor, Mark S., et al.: "Enantioselective Michael additions to a,β-unsaturated imides catalyzed by a Salen-Al complex," Sep. 2003 vol. 125, Issue 37, 11204-11205.

Nakano, Koji, et al.: "Selective Formation of Polycarbonate over Cyclic Carbonate: Copolymerization of Epoxides with Carbon Dioxide Catalyzed by a Cobalt(III) Complex with a Piperidinium End-Capping Arm," Chem. Int. Ed. 2006, vol. 45, 7274-7277, Wiley-VCH Verlag GmbH & Co. KGaA, Weinheim.

Maroto, A., et al.: "Relationship between surface properties of PtSn±SiO2 catalysts and their catalytic performance for the CO2 and propylene reaction to yield hydroxybutanoic acid," Appl. Organometal. Chem. 2000, vol. 14, 783-788, John Wiley & Sons, Ltd.

Balskus, Emily P., et al.: "a,β-Unsaturated β-Silyl Imide Substrates for Catalytic, Enantioselective Conjugate Additions: A Total Synthesis of (+)-Lactacystin and the Discovery of a New Proteasome Inhibitor," J.. Am. Chem. Soc. 2006, vol. 128, 6810-6812, American Chemical Society.

Sung-Suh, Hyung Mi, et al.: "Photoinduced activation of CO2 by rhenium complexes encapsulated in molecular sieves," Appl. Organometal. Chem. 2000 vol. 14, 826-830, John Wiley & Sons, Ltd.

Kosugi, Yoshio, et al.: "Carboxylation of alkali metal phenoxide with carbon dioxide at terrestrial temperature," Appl. Organometal. Chem. 2000, vol. 14, 841-843, John Wiley & Sons, Ltd.

Ballivet-Tkatchenko, Danielle, et al.: "Electrocatalytic reduction of CO2 for the selective carboxylation of olefins," Appl. Organometal. Chem., 2000, vol. 14, 847-849, John Wiley & Sons, Ltd.

Tanaka, Koji, et al.: "Selective formation of ketones by electrochemical reduction of CO2 catalyzed by ruthenium complexes," Appl. Organometal. Chem., 2000, vol. 14, 863-866, John Wiley & Sons, Ltd.

Styring, Peter, et al.: "A polymer-supported nickel(II) catalyst for room temperature Tamao-Kumada-Corriu coupling reactions," Catalysis Letters 2001, vol. 77, No. 4, Plenum Publishing Corporation.

Molnar, Ferenc, et al.: Multisite Catalysis: A Mechanistic Study of β-Lactone Synthesis from Epoxides and CO-Insights into a Difficult Case of Homogeneous Catalysis, Chem. Eur. J., 2003, vol. 9, No. 6, 1273-1280, Wiley-VCH Verlag GmbH & Co. KGaA, Weinheim.

Phan, Nam, T.S., et al.: "Solid-supported cross-coupling catalysts derived from homogeneous nickel and palladium coordination complexes," Appl. Organometal Chem., 2000, vol. 14, 794-798, The Royal Society of Chemistry, UK.

Shen, Yu-Mei, "Chemical Fixation of Carbon Dioxide Co-Catalyzed by a Combination of Schiff Bases or Phenols and Organic Bases," Eur. J. Org. Chem. 2004, 3080-3089, Wiley-VCH Verlag GmbH & co. KGaA, Weinheim.

Braunstein, Pierre, et al.: "Carbon Dioxide Activation and Catalytic Lactone Synthesis by Telomerization of Butadiene and C02," J. Am. Chem. Soc., 1988, vol. 110, 3207-3212, American Chemical Society.

Tsuda, Tetsuo, et al.: "Nickel(0)-Catalyzed Alternating Copolymerization of Carbon Dioxide with Diynes to Poly ( 2-pyrones)," J. Am. Chem. Soc. 1992, vol. 114, 1498-1499, American Chemical Society.

Hoffman, William A., III: "Convenient Preparation of Carbonates from Alcohols and Carbon Dioxide," J. Org. Chem. 1982, vol. 47, 5209-5210, American Chemical Society.

Tsuda, Tetsuo, et al.: "Nickel(O)-Catalyzed Cycloaddition of Diynes and Carbon Dioxide to Bicyclic α-Pyrones," J. Org. Chem. 1988, vol. 53, 3140-3145, American Chemical Society.

Shi, Min, et al.: "Transition-Metal-Catalyzed Reactions of Propargylamine with Carbon Dioxide and Carbon Disulfide," J. Org. Chem. 2002, vol. 67, 16-21, American Chemical Society.

Lefeber, C., et al.: "Regioselektive Reaktionen der fremdligandfreien Titanocen-Alkin-Komplexe Cp,Ti( RC,SiMe,) (R = Me,3, Ph, 1Bu, nBu)," J. Organometallic Chemistry, 1995 vol. 501, 179-188, Elsevier Science S.A.

Tsuda, Tetsuo, et al.: "Nickel(0)-Catalyzed Cycloaddition Copolymerization of Ether Diynes with Carbon Dioxide to Poly(2-pyrone)s," Macromolecules 1996, vol. 28, 1356-1359, American Chemical Society.

(56) References Cited

OTHER PUBLICATIONS

McGee, William, et al.: "Palladium-Catalyzed Generation of 0-Allylic Urethanes and Carbonates from Amines/ Alcohols, Carbon Dioxide, and Allylic Chlorides," Organometallics 1993, vol. 12, 1429-1433, American Chemical Society.
Bartoli, Giuseppe, et al.: "Direct Catalytic Synthesis of Enantiopure 5-Substituted Oxazolidinones from Racemic Terminal Epoxides," Organic Letters 2005, vol. 7, No. 10, 1983-1985, American Chemical Society.
Mizojiri, Ryo, et al.: Regioselectivity in the nickel-catalysed coupling of cyclic carbonates of but-3-ene-1,2-diols with organoborates, J. Chem. Soc. Perkin Trans. 1995, 2073-2075.
Gholamkhass, Bobak, et al.: "Architecture of Supramolecular Metal Complexes for Photocatalytic $CO_2$ Reduction: Ruthenium-Rhenium Bi- and Tetranuclear Complexes," Inorganic Chemistry, 2005, vol. 44, No. 7, American Chemical Society.
Takavec, Thomas N., et al.: "Regioselectivity in nickel(0) catalyzed cycloadditions of carbon dioxide with diynes," Tetrahedron 60, 2004, 7431-7437, Elsevier Ltd. UK.
Phan, Nam T.S., et al.: "Polymer-supported palladium catalysed Suzuki—Miyaura reactions in batch and a mini-continuous flow reactor system," Tetrahedron 61, 2005, 12065-12073, Elsevier Science Ltd. UK.
Matsumoto, Kazutsugu, et al.: "Enzyme-Mediated Enantioselective Hydrolysis of Cyclic Carbonates," Tetrahedron Letters, 1995, vol. 36, No. 36, 6499-6502, Elsevier Science Ltd. UK.
Chang, Han-Ting, et al.: "A Practical Route to Enantiopure 1,2-Aminoalcohols." Tetrahedron Letters, 1996, vol. 37, No. 19, 3219-3222, Elsevier Science Ltd. UK.
Schultze, Lisa M., et al.: "Practical Synthesis of the anti-HIV Drug, PMPA," Tetrahedron Letters 39, 1998, 1853-1856, Elsevier Science Ltd. UK.
S. Jegham, et al.: "Use of Chiral Glycerol 2,3-Carbonate in the Synthesis of 3-Aryl-2-oxazolidinones," Tetrahedron Letters 39, 1998, 4453-4454, Elsevier Science Ltd. UK.
Phan, Nam, T.S., et al.: "A polymer-supported salen-type palladium complex as a catalyst for the Suzuki—Miyaura cross-coupling reaction," Tetrahedron Letters 45, 2004, 7915-7919, Elsevier Science Ltd. UK.
Hu, Shaojing, et al., "An Efficient Synthesis of (+)-exo-Brevicomin via Chloroallylboration", J. Org. Chem. 1999, 64, 2524-2526.
Huang, Jin-Wen, et al., "Chemical Fixation of Carbon Dioxide by NaI/PPh3/PhOH", J. Org. Chem. 2003, 68, 6705-6709.
Jiang, Jia-Li, et al., "Re(CO)5Br-Catalyzed Coupling of Epoxides with $CO_2$ Affording Cyclic Carbonates under Solvent-Free Conditions", J. Org. Chem. 2005, 70, 381-383.
Kim, Yong Jin, et al., "Tetrahaloindate(III)-Based Ionic Liquids in the Coupling Reaction of Carbon Dioxide and Epoxides to Generate Cyclic Carbonates: H-Bonding and Mechanistic Studies", J. Org. Chem. 2005, 70, 7882-7891.
Sit, Wing Nga, et al., "Coupling Reactions of $CO_2$ with Neat Epoxides Catalyzed by PPN Salts to Yield Cyclic Carbonates", J. Org. Chem. 2005, 70, 8583-8586.
Lu, Xiao-Bing, et al., "Aluminum phthalocyanine complex covalently bonded to MCM-41 silica as heterogeneous catalyst for the synthesis of cyclic carbonates", Journal of Molecular Catalysis A: Chemical 186 (2002) 33-42.
Doskocil, Eric J., et al., "UV-Vis Spectroscopy of Iodine Adsorbed on Alkali-Metal-Modified Zeolite Catalysts for Addition of Carbon Dioxide to Ethylene Oxide", J. Phys. Chem. B 1999, 103, 6277-6282.
Peng, Jiajian, et al., "Cycloaddition of carbon dioxide to propylene oxide catalyzed by ionic liquids", New J. Chem., 2001, 25, 639-641.
Xie, Haibo, et al., "The effective synthesis of propylene carbonate catalyzed by silica-supported hexaalkylguanidinium chloride", New J. Chem., 2005, 29, 1199-1203.
Calo, Vincenzo, et al., "Cyclic Carbonate Formation from Carbon Dioxide and Oxiranes in Tetrabutylammonium Halides as Solvents and Catalysts", American Chemical Society, Published on Web Jun. 29, 2002.
Berkessel, Albrecht, et al., "Catalytic Asymmetric Addition of Carbon Dioxide to Propylene Oxide with Unprecedented Enantioselectivity", American Chemical Society, Published on Web Aug. 26, 2006.
Zhao, Tiansheng, et al., "Cycloaddition between propylene oxide and $CO_2$ over metal oxide supported KI", Phys. Chem. Chem. Phys., 1999, 1, 3047-3051.
Kasuga, Kuninobu, et al., "Cycloaddition of Carbon Dioxide to Propylene Oxide Catalysed by Tetra-t-Butylphthalocyaninatoaluminium(III) Chloride", Polyhedron vol. 15, No. 1, pp. 69-72, 1996.
Sakharov, A.M., et al., "Copolymerization of propylene oxide with carbon dioxide catalyzed by zinc adipate", Russian Chemical Bulletin, International Edition, vol. 51, No. 8, pp. 1451-1454, Aug. 2002.
Lermontov, S.A., et al., "8-Hydroxyquinolates of trivalent metals as new catalysts for the reaction of $CO_2$ with epoxides", Russian Chemical Bulletin, International Edition, vol. 51, No. 5, pp. 836-838, May 2002.
Rybina, G.V., et al., "Synthesis of Cyclic Organic Carbonates from C3C16 Epoxides", Russian Journal of Applied Chemistry, vol. 76, No. 5, 2003, pp. 842-843. Translated from Zhumal Prikladnoi Khimii, vol. 76, No. 5, 2003, pp. 870-871.
Lermontov, S.A., et al., "Aluminum 8-Hydroxyquinolate, A New Catalyst for $CO_2$ Reactions with Epoxides", Russian Journal of General Chemistry, vol. 72, No. 9, 2002, pp. 1492-1493. Translated from Zhurnal Obshchei Khimii, vol. 72, No. 9, 2002, pp. 1581-1582.
Zaitseva, V.V., et al., "Synthesis and Structure of 8-Methyl-2-methylene-1,4,6,9-tetraoxaspiro[4.4]nonane", Russian Journal of Organic Chemistry, vol. 38, No. 4, 2002, pp. 588-590. Translated from Zhumal Organicheskoi Khimii, vol. 38, No. 4, 2002, pp. 614-616.
Jiang, Jia-Li, et al., "Efficient DMF-Catalyzed Coupling of Epoxides with $CO_2$ under Solvent-Free Conditions to Afford Cyclic Carbonates", Synthetic Communicationsw, 36: 3141-3148, 2006.
Brunner, M., et al., "Kinetic Resolution of Oxiranes by Use of Chiral Lewis Acid Catalysts", Institute of Technical Chemistry and Petrolchemistry. RWTH Aachen, Templergraben 55. 52056 Aachen, FRO Synlett, vol. 12, 1993, pp. 893-894.
Tascedda, Patricia, et al., "Electrosynthesis of Benzolactones by Nickel-Catalyzed Carboxylation of Epoxide-Functionalized Aromatic Halides", Synlett 2000, No. 2, 245-247 ISSN 0936-5214.
Qi, Charorong, et al., "Naturally Occurring a-Amino Acid Catalyzed Coupling of Carbon Dioxide with Epoxides to Afford Cyclic Carbonates", Synlett 2007, No. 2, pp. 0255-025801.02.207, Advanced online publication: Jan. 24, 2007.
Ochiai, Bungo, et al., "Kinetic and computational studies on aminolysis of bicyclic carbonates bearing alicyclic structure giving alicyclic hydroxyurethanes", Science Direct, Tetrahedron 61 (2005) 1835-1838.
Rodriguez, A., et al., "Total synthesis of lipoxin A4 and lipoxin B4 from butadiene", Tetrahedron Letters 41 (2000) 823-826.
Barbarini, Alessandro, et al., "Cycloaddition of $CO_2$ to epoxides over both homogeneous and silica-supported guanidine catalysts", Tetrahedron Letters 44 (2003) 2931-2934.
Paddock, Robert L., et al., "Co(III) porphyrin/DMAP: an efficient catalyst system for the synthesis of cyclic carbonates from $CO_2$ and epoxides", Science Direct, Tetrahedron Letters 45 (2004) 2023-2026.
Li, Fuwei, et al., "Chemical fixation of $CO_2$ with highly efficient ZnCl2/[BMIm]Br catalyst system", Science Direct, Tetrahedron Letters 45 (2004) 8307-8310.
Du, Ya, et al., "A poly(ethylene glycol)-supported quaternary ammonium salt for highly efficient and environmentally friendly chemical fixation of $CO_2$ with epoxides under supercritical conditions", Science Direct, Tetrahedron Letters 47 (2006) 1271-1275.
Chen, Shu-Wei, et al., "Efficient catalytic synthesis of optically active cyclic carbonates via coupling reaction of epoxides and carbon dioxide", Science Direct, Tetrahedron Letters 48 (2007) 297-300.
Lu, Xiao-Bing, et al., "Catalytic formation of ethylene carbonate from supercritical carbon dioxide/ethylene oxide mixture with tetradentate Schiff-base complexes as catalyst", Applied Catalysis A: General 234 (2002) 25-33.

(56) References Cited

OTHER PUBLICATIONS

Lu, Xiao-Bing, et al., "Chemical fixation of CO2 to ethylene carbonate under supercritical conditions: continuous and selective", Applied Catalysis A: General 275 (2004) 73-78.

Paddock, Robert L., et al., "Chiral (salen)CoIII catalyst for the synthesis of cyclic carbonates", Chem. Commun., 2004, 1622-1623.

Jing, Huanwang, et al., "(Salen)Tin Complexes: Syntheses, Characterization, Crystal Structures, and Catalytic Activity in the Formation of Propylene Carbonate from CO2 and Propylene Oxide", Inorg. Chem. 2004, 43, 4315-4327.

Chen, Peter, et al., "Binding of Propylene Oxide to Porphyrin- and Salen-M(III) Cations, Where M ) Al, Ga, Cr, and Co", Inorg. Chem. 2005, 44, 2588-2595.

Darensbourg, Donald J., et al., "Comparative Kinetic Studies of the Copolymerization of Cyclohexene Oxide and Propylene Oxide with Carbon Dioxide in the Presence of Chromium Salen Derivatives. In Situ FTIR Measurements of Copolymer vs Cyclic Carbonate Production", JACS Articles, Published on Web Jun. 3, 2003, J. Am. Chem. Soc. 2003, 125, 7586-7591.

Lu, Xiao-Bing, et al., "Asymmetric Catalysis with CO2: Direct Synthesis of Optically Active Propylene Carbonate from Racemic Epoxides", JACS Communications, Published on Web Mar. 5, 2004, J. Am. Chem. Soc. 2004, 126, 3732-3733.

Lu, Xiao-Bing, et al., "Highly active electrophile—nucleophile catalyst system for the cycloaddition of CO2 to epoxides at ambient temperature", Science Direct, Journal of Catalysis 227 (2004) 537-541.

Alvaro, Mercedes, et al., "CO2 fixation using recoverable chromium salen catalysts: use of ionic liquids as cosolvent or high-surface-area silicates as supports", Science Direct, Journal of Catalysis 228 (2004) 254-258.

Lu, Xiao-Bing, et al., "Synthesis of ethylene carbonate from supercritical carbon dioxide/ethylene oxide mixture in the presence of bifunctional catalyst", Journal of Molecular Catalysis A: Chemical 186 (2002) 1-11.

Lu, Xiao-Bing, et al., "Chemical fixation of carbon dioxide to cyclic carbonates under extremely mild conditions with highly active bifunctional catalysts", Science Direct, Journal of Molecular Catalysis A: Chemical 210 (2004) 31-34.

Alvaro, Mercedes, et al., "Polymer-bound aluminium salen complex as reusable catalysts for CO2 insertion into epoxides", Science Direct, Tetrahedron 61 (2005) 12131-12139.

Kroger, Mario, et al., "Alternating Copolymerization of Carbon Dioxide and Cyclohexene Oxide and Their Terpolymerization with Lactide Catalyzed by Zinc Complexes of N,N Ligands", Adv. Synth. Catal. 2006, 348, 1908-1918.

Lu, Xiao-Bing, et al., "Highly Active, Binary Catalyst Systems for the Alternating Copolymerization of CO2 and Epoxides under Mild Conditions", Angew. Chem. Int. Ed. 2004, 43, 3574-3577.

Darensbourg, Donald J., et al., "Probing the mechanistic aspects of the chromium salen catalyzed carbon dioxide/epoxide copolymerization process using in situ ATR/FTIR", Science Direct, Catalysis Today 98 (2004) 485-492.

Stamp, Louise M., et al., "Polymer supported chromium porphyrin as catalyst for polycarbonate formation in supercritical carbon dioxide", Chem. Commun., 2001, 2502-2503.

Darensbourg, Donald J., et al., "Solid-State Structures of Zinc(II) Benzoate Complexes. Catalyst Precursors for the Coupling of Carbon Dioxide and Epoxides", Inorg. Chem. 2002, 41, 973-980.

North M., Young C. Bimetallic aluminium(acen) complexes as catalysts for the synthesis of cyclic carbonates from carbon dioxide and epoxides. Catalysis Science & Technology 2011, 1(1),93-99.

Meléndez, J., North M, Villuendas P, Young C. One-component bimetallic aluminium(salen)-based catalysts for cyclic carbonate synthesis and their immobilization. Dalton Transactions 2011, 40(15), 3885-3902.

Darensbourg, Donald J., et al., "The Copolymerization of Carbon Dioxide and [2-(3,4-Epoxycyclohexyl)ethyl] trimethoxysilane Catalyzed by (Salen)CrCl. Formation of a CO2 Soluble Polycarbonate", Inorg. Chem. 2003, 42, 4498-4500.

Darensbourg, Donald J., et al., "Cyclohexene Oxide/CO2 Copolymerization Catalyzed by Chromium(III) Salen Complexes and N-Methylimidazole: Effects of Varying Salen Ligand Substituents and Relative Cocatalyst Loading", Inorg. Chem. 2004, 43, 6024-6034.

Darensbourg, Donald J., et al., "Aluminum Salen Complexes and Tetrabutylammonium Salts: A Binary Catalytic System for Production of Polycarbonates from CO2 and Cyclohexane Oxide", Inorg. Chem. 2005, 44, 1433-1442.

Darensbourg, Donald J., et al., "Effective, Selective Coupling of Propylene Oxide and Carbon Dioxide to Poly(Propylene Carbonate) Using (Salen)CrN3 Catalysts", Inorg. Chem. 2005, 44, 4622-4629.

Darensbourg, Donald J., et al., "Syntheses and Structures of Epoxide Adducts of Soluble Cadmium(I1) Carboxylates. Models for the Initiation Process in EpoxideKOz Coupling Reactions", J. Am. Chem. Soc. 1995,117, 538-539.

Cheng, Ming, et al., "Catalytic Reactions Involving C1 Feedstocks: New High-Activity Zn(II)-Based Catalysts for the Alternating Copolymerization of Carbon Dioxide and Epoxides", J. Am. Chem. Soc. 1998, 120, 11018-11019.

Darensbourg, Donald J., et al., "Bis 2,6-difluorophenoxide Dimeric Complexes of Zinc and Cadmium and Their Phosphine Adducts: Lessons Learned Relative to Carbon Dioxide/Cyclohexene Oxide Alternating Copolymerization Processes Catalyzed by Zinc Phenoxides", J. Am. Chem. Soc. 2000, 122, 12487-12496.

Allen, Scott D., et al., "High-Activity, Single-Site Catalysts for the Alternating Copolymerization of CO2 and Propylene Oxide", JACS Communications, Published on Web Nov. 8, 2002, J. Am. Chem. Soc. 2002, 124, 14284-14285.

Darensbourg, Donald J., et al., "Mechanistic Aspects of the Copolymerization Reaction of Carbon Dioxide and Epoxides, Using a Chiral Salen Chromium Chloride Catalyst", JACS Articles, J. Am. Chem. Soc. 2002, 124, 6335-6342.

Lu, Xiao-Bing, et al, "Design of Highly Active Binary Catalyst Systems for CO2/Epoxide Copolymerization: Polymer Selectivity, Enantioselectivity, and Stereochemistry Control", JACS Articles, J. Am. Chem. Soc. 2006, 128, 1664-1674.

Darensbourg, Donald J., et al., "Supercritical carbon dioxide as solvent for the copolymerization of carbon dioxide and propylene oxide using a heterogeneous zinc carboxylate catalyst", Journal of Molecular Catalysis A: Chemical 104 ( 1995) L1-L4.

Walther, Martin, et al., "Synthesis of Azolyl Carboximidamides as Ligands for Zn(II) and Cu(II): Application of the Zn(II) Complexes as Catalysts for the Copolymerization of Carbon Dioxide and Epoxides1", JOC Article, J. Org. Chem. 2006, 71, 1399-1406.

Darensbourg, Donald J., et al., "Catalytic Activity of Zinc(I1) Phenoxides Which Possess Readily Accessible Coordination Sites. Copolymerization and Terpolymerization of Epoxides and Carbon Dioxide", American Chemical Society, Macromolecules 1995,28, 7577-7579.

Mang, Stephan, et al., "Copolymerization of CO2 and 1,2-Cyclohexene Oxide Using a CO2-Soluble Chromium Porphyrin Catalyst", American Chemical Society, Macromolecules 2000, 33, 303-308.

Darensbourg, Donald J., et al., "Pressure Dependence of the Carbon Dioxide/Cyclohexene Oxide Coupling Reaction Catalyzed by Chromium Salen Complexes. Optimization of the Comonomer-Alternating Enchainment Pathway", American Chemical Society, Organometallics 2005, 24, 144-148.

Darensbourg, Donald J., et al., "Copolymerization of CO2 and Epoxides Catalyzed by Metal Salen Complexes", Acc. Chem. Res. 2004, 37, 836-844.

Coates, Geoffrey W., et al., "Discrete Metal-Based Catalysts for the Copolymerization of CO2 and Epoxides: Discovery, Reactivity, Optimization, and Mechanism", Angew. Chem. Int. Ed. 2004, 43,6618-6639.

Baiker, Alfons, "Utilization of carbon dioxide in heterogeneous catalytic synthesis", Applied Organometallic Chemistry, Appl. Organometal. Chem. 14, 751-762 (2000).

"The contribution of the utilization option to reducing the CO2 atmospheric loading: research needed to overcome existing barriers for a full exploitation of the potential of the CO2 use", Science Direct, Catalysis Today 98 (2004) 455-462.

(56) References Cited

OTHER PUBLICATIONS

Omae, Iwao, "Aspects of carbon dioxide utilization", Science Direct, Catalysis Today 115 (2006) 33-52.
Zevenhoven, Ron, et al., "Chemical fixation of CO2 in carbonates: Routes to valuable products and long-term storage", Science Direct, Catalysis Today 115 (2006) 73-79.
Yoshida, M., et al., Synthesis of Cyclic Carbonates, Recycling of CO2, Chem. Eur. J. 2004, 10, 2886-2893.
Braunstein, Pierre, et al., "Reactions of Carbon Dioxide with Carbon-Carbon Bond Formation Catalyzed by Transition-Metal Complexes", American Chemical Society, Chem. Rev. 1980, 88, 747-764.
Gibson, Dorothy H., "The Organometallic Chemistry of Carbon Dioxide", American Chemical Society, Chem. Rev. 1996, 96, 2063-2095.
Shaikh, Abbas-Alli G., "Organic Carbonates", American Chemical Society, Chem. Rev. 1996, 96, 951-976.
Arakawa, Hironori, et al., "Catalysis Research of Relevance to Carbon Management: Progress, Challenges, and Opportunities", American Chemical Society, Chem. Rev. 2001, 101, 953-996.
Dell'Amico, Daniela Belli, et al., "Converting Carbon Dioxide into Carbamato Derivatives", American Chemical Society, Chem. Rev. 2003, 103, 3857-3897.
Darensbourg, Donald J., et al., "Catalysts for the reactions of epoxides and carbon dioxide", Coordination Chemistry Reviews, 153 (1996) 155-174.
Leitner, W., "The coordination chemistry of carbon dioxide", Coordination Chemistry Reviews, 153 (1996) 257-284.
Ungvary, Ferenc, Application of transition metals in hydroformylation. Annual survey covering the year 1995, Coordination Chemistry Reviews, 160 (1997) 129-159.
Ungvary, Ferenc, Application of transition metals in hydroformylation: annual survey covering the year 1996, Coordination Chemist Reviews, 167 (1997) 233-260.
Ungvary, Ferenc, "Hydroformylation", Coordination Chemist Reviews, 170 (1998) 245-281.
Yin, Xiaolong, et al., "Recent developments in the activation of carbon dioxide by metal complexes", Coordination Chemistry Reviews, 181 (1999) 27-59.
Walther, Dirk, et al., "Carbon dioxide and metal centres: from reactions inspired by nature to reactions in compressed carbon dioxide as solvent", Coordination Chemistry Reviews, 182 (1999) 67-100.
Tanaka, Koji, et al., "Multi-electron reduction of CO2 via Ru-CO2, -C(O)OH, -CO, -CHO, and -CH2OH species", Coordination Chemistry Reviews 226 (2002) 211-218.
Ungvary, Ferenc, "Application of transition metals in hydroformylation annual survey covering the year 2001", Coordination Chemistry Reviews 228 (2002) 61-82.
Ungvary, Ferenc, "Application of transition metals in hydroformylation annual survey covering the year 2002", Science Direct, Coordination Chemistry Reviews 241 (2003) 295-312.
Jessop, Philip G., et al., "Recent advances in the homogeneous hydrogenation of carbon dioxide", Science Direct, Coordination Chemistry Reviews 248 (2004) 2425-2442.
Ungvary, Ferenc, "Application of transition metals in hydroformylation annual survey covering the year 2003", Science Direct, Coordination Chemistry Reviews 248 (2004) 867-880.
Xiaoding, Xu, et al., "Mitigation of CO2 by Chemical Conversion: Plausible Chemical Reactions and Promising Products", American Chemical Society, Energy & Fuels 1996, 10, 305-325.
Pacheco, Michael A., et al., "Review of Dimethyl Carbonate (DMC) Manufacture and its Characteristics as a Fuel Additive", American Chemical Society, Energy & Fuels 1997, 11, 2-29.
"Green Chemical Processing Using CO2", American Chemical Society, Ind. Eng. Chem. Res. 2003, 42, 1598-1602.
Sun, Jianmin, et al., "Development in the green synthesis of cyclic carbonate from carbon dioxide using ionic liquids", Science Direct, Journal of Organometallic Chemistry 690 (2005) 3490-3497.
Sugimoto, Hiroshi, et al., "Copolymerization of Carbon Dioxide and Epoxide", Journal of Polymer Science: Part A: Polymer Chemistry, vol. 42, 5561-5573 (2004).
Carmona, Ernesto, et al., "Electron-rich metal complexes for C0O2 and CS2 incorporation", Pure & Appl. Chem., vol. 61, No. 10, pp. 1701-1706, 1989.
Aresta, Michele, "Carbon dioxide asa building-block for molecular organic compounds", The Chemical Society, RSC Wokshop, Burlington House, Jul. 27, 2006.
Rayner, Prof. Chris, "Converting carbon dioxide to chemicals", Burlington House, Jul. 27, 2006, RSC Advancing the Chemical Sciences.
Green, Malcolm, "Converting CO2 into Chemicals", RSC Environment, Sustainability and Energy Forum, Oxford University, Jul. 2006.
Hall, Peter, et al., "Converting CO2 Into Fuels and Chemicals: The Formic Acid Economy" (2006).
Taylor, Mark S., et al., "Highly Enantioselective Conjugate Additions to r,â-Unsaturated Ketones Catalyzed by a (Salen)Al Complex", JACS Articles, Published on Web Jan. 6, 2005.
Maggi, Raimondo, et al., "Synthesis of oxazolidinones in supercritical CO2 under heterogeneous catalysis", Science Direct, Tetrahedron Letters 48 (2007) 2131-2134.
Saito, Mashairo, et al., "Advances in joint research between NIRE and RITE for developing a novel technology for methanol synthesis from CO2 and H2", Applied Organometallic Chemistry Appl. Organometal. Chem. 14, 763-772 (2000).
Nam, Sang-Sung, et al., "Effect of lanthanum loading in Fe±K/La±Al2O3 catalysts for CO2 hydrogenation to hydrocarbons", Applied Organometallic Chemistry Appl. Organometal. Chem. 14, 794-798 (2000).
Ushikoshi, Kenji, et al., "Methanol synthesis from CO2 and H2 in a bench-scale test plant", Applied Organometallic Chemistry Appl. Organometal. Chem. 14, 819-825 (2000).
Ando, Hisanori, et al., "Active phase of iron catalyst for alcohol formation in hydrogenation of carbon oxides", Applied Organometallic Chemistry Appl. Organometal. Chem. 14, 831-835 (2000).
Kusama, Hitoshi, et al., "Alcohol synthesis by catalytic hydrogenation of CO2 over Rh±Co/SiO2", Applied Organometallic Chemistry Appl. Organometal. Chem. 14, 836, 840 (2000).
Joo, Ferenc, et al., "Note Homogeneous hydrogenation of aqueous hydrogen carbonate to formate under mild conditions with water soluble rhodium(I)± and ruthenium(II)±phosphine catalysts", Applied Organometallic Chemistry Appl. Organometal. Chem. 14, 857-859 (2000).
Shen, Yu-Mei, et al., "Phenol and Organic Bases Co-Catalyzed Chemical Fixation of Carbon Dioxide with Terminal Epoxides to Form Cyclic Carbonates", State Key Laboratory of Organometallic Chemistry, Shanghai Institute of Organic Chemistry, Chinese Academy of Sciences, 354 Fenglin Lu, Shanghai 200032, P. R. China (2003).
Kim, Hoon Sik, et al., Isolation of a Pyridinium Alkoxy Ion Bridged Dimeric Zinc complex for the Coupling Reactions of CO2 and Epoxides, Angew. Chem. Int. Ed. 2000, 39, No. 22.
Aresta, Michele, et al., "Direct synthesis of organic carbonates by oxidative carboxylation of ole®ns catalyzed by metal oxides: developing green chemistry based on carbon dioxide", Applied Organometallic Chemistry Appl. Organometal. Chem. 14, 799-802 (2000).
Sun, Jianmin, et al., "Direct oxidative carboxylation of styrene to styrene carbonate in the presence of ionic liquids", Science Direct, Catalysis Communications 5 (2004) 83-87.
Vieville, C., et al., "Synthesis of glycerol carbonate by direct carbonatation of glycerol in supercritical CO2 in the presence of zeolites and ion exchange resins", Catalysis Letters 56 (1998) 245-247.
Srivastava, R., et al., "Synthesis of polycarbonate precursors over titanosilicate molecular sieves", Catalysis Letters vol. 91, Nos. 1-2, Nov. 2003 (# 2003).
Sun, Jianmin, et al., "One-pot synthesis of styrene carbonate from styrene in tetrabutylammonium bromide", Science Direct, Catalysis Today 93-95 (2004) 383-388.
Dibenedetto, Angela, et al., "Synthesis of cyclic carbonates from epoxides: Use of reticular oxygen of Al2O3 or Al2O3-supported

(56) References Cited

OTHER PUBLICATIONS

CeOx for the selective epoxidation of propene", Science Direct, Catalysis Today 115 (2006) 117-123.

Kisch, Horst, et al., "Bifunktionelle Katalysatoren zur Synthese cyclischer Carbonate aus Oxiranen and Kohlendioxid", Chem. Ber. 119. 1095-1100 (1986).

Tominaga, Ken-Ichi, et al., "Ethylene Oxide-mediated Reduction of C02 to CO and Ethylene Glycol catalysed by Ruthenium Complexes", J. Chem. Soc., Chem. Commun., 1995.

Tascedda, Patricia, et al., "Novel Electrochemical Reactivity of Ni(cyclam)Br2: Catalytic Carbon Dioxide Incorporation into Epoxides", J. Chem. Soc., Chem. Commun., 1995.

Yano, Takashi, et al., "Magnesium oxide-catalysed reaction of carbon dioxide with an epoxide with retention of stereochemistry", pp. 1129-1130, Chem. Commun., 1997.

Kawanami, Hajime, et al., "Chemical fixation of carbon dioxide to styrene carbonate under supercritical conditions with DMF in the absence of any additional catalysts", Chem. Commun., 2000, 2089-2090.

Yang, Hongzhou, et al., "Electrochemical activation of carbon dioxide in ionic liquid: synthesis of cyclic carbonates at mild reaction conditions", Chem. Commun. , 2002, 274-275.

Kawanami, Hajime, et al., "A rapid and effective synthesis of propylene carbonate using a supercritical CO2—ionic liquid system", Chem. Commun. , 2003, 896-897.

Mori, Kohsuke, et al., "A single-site hydroxyapatite-bound zinc catalyst for highly efficient chemical fixation of carbon dioxide with epoxides", Chem. Commun., 2005, 3331-3333.

Takahashi, Toshikazu, et al., "Synergistic hybrid catalyst for cyclic carbonate synthesis: Remarkable acceleration caused by immobilization of homogeneous catalyst on silica", Chem. Commun., 2006, 1664-1666.

Kim, Hoon Sik, et al., "New Mechanistic Insight into the Coupling Reactions of CO2 and Epoxides in the Presence of Zinc Complexes", Chem. Eur. J. 2003, 9, No. 3.

Man, Lok Man, et al., "Synthesis of Heterobimetallic RuMn Complexes and the Coupling Reactions of Epoxides with Carbon Dioxide Catalyzed by these Complexes", Chem. Eur. J. 2006, 12, 1004-1015.

Takata, Toshikazu, et al., "Synthesis of Calix[4]arene and Porphyrin Tethering Four Chiral Five-Membered Cyclic Carbonates", Enantiomer, vol. 7, pp. 129-132 (2002).

Aresta, Michele, et al., "Unique Evidence for a RhIII to RhI Reduction by Deoxygenation of a Carbonate Moiety to CO2 by an Out-of-Sphere Phosphane", Eur. J. Inorg. Chem. 2001, 180121806.

Solladie-Cavallo, Arlette, et al., "A Mild Stereo- and Enantiospecific Conversion of 2,3-Diaryl-Substituted Oxiranes into 2,2-Dimethyl-1,3-Dioxolanes by an Acetone/Amberlyst 15 System", Eur. J. Org. Chem. 2006, 3007-3011.

Sako, Takeshi, et al., "Cycloaddition of Oxirane Group with Carbon Dioxide in the Supercritical Homogeneous State", Ind. Eng. Chem. Res. 2002, 41, 5353-5358.

Aida, Takuzo, et al., "Activation of Carbon Dioxide with Aluminum Porphyrin and Reaction with Epoxide. Studies on (Tetraphenylporphinato)aluminum Alkoxide Having a Long Oxyalkylene Chain as the Alkoxide Group", J. Am. Chem. Soc. 1983, 105, 1304-1309.

Trost, Barry M., et al., Palladium-Mediated Vicinal Cleavage of Allyl Epoxides with Retention of Stereochemistry: A Cis Hydroxylation Equivalent, J. Am. Chem. Soc. 1985, 107, 6123-6124.

Myers, Andrew G., "Stereochemical Assignment of Neocarzinostatin Chromophore. Structures of Neocarzinostatin Chromophore-Methyl Thioglycolate Adductst", J. Am. Chem. Soc. 1988, 110, 7212-7214.

Sugimoto, Hiroshi, et al., "Photoresponsive Molecular Switch to Control Chemical Fixation of CO2", J. Am. Chem. Soc. 1999, 121, 2325-2326.

Yamaguchi, Kazuya, et al., "Mg-Al Mixed Oxides as Highly Active Acid-Base Catalysts for Cycloaddition of Carbon Dioxide to Epoxides", J. Am. Chem. Soc. 1999, 121, 4526-4527.

Paddock, Robert L., et al., "Chemical CO2 Fixation: Cr(III) Salen Complexes as Highly Efficient Catalysts for the Coupling of CO2 and Epoxides", J. Am. Chem. Soc. 2001, 123, 11498-11499.

Shi, Feng, et al., "From CO Oxidation to CO2 Activation: An Unexpected Catalytic Activity of Polymer-Supported Nanogold", JACS Communications, Published on Web Mar. 4, 2005.

Doll, Kenneth M., et al., "Synthesis of Carbonated Fatty Methyl Esters Using Supercritical Carbon Dioxide", J. Agric. Food Chem. 2005, 53, 9608-9614.

Tu, Mai, et al., "Cycloaddition of CO2 to Epoxides over Solid Base Catalysts", Journal of Catalysis 199, 85-91 (2001).

Kim, Hoon Sik, et al., "Well-Defined Highly Active Heterogeneous Catalyst System for the Coupling Reactions of Carbon Dioxide and Epoxides", Journal of Catalysis 205, 226-229 (2002).

Yasuda, Hiroyuki, et al., "Cyclic Carbonate Synthesis from Supercritical Carbon Dioxide and Epoxide over Lanthanide Oxychloride", Journal of Catalysis 209, 547-550 (2002).

Sun, Jianmin, et al., "A direct synthesis of styrene carbonate from styrene with the Au/SiO2—ZnBr2/Bu4NBr catalyst system", Science Direct, Journal of Catalysis 230 (2005) 398-405.

Yasuda, Hiroyuki, et al., "Efficient synthesis of cyclic carbonate from carbon dioxide catalyzed by polyoxometalate: the remarkable effects of metal substitution", Science Direct, Journal of Catalysis 233 (2005) 119-122.

Srivastava, R., et al., "CO2 activation and synthesis of cyclic carbonates and alkyl/aryl carbamates over adenine-modified Ti-SBA-15 solid catalysts", Science Direct, Journal of Catalysis 233 (2005) 1-15.

Aresta, Michele, et al., "Carbon dioxide as building block for the synthesis of organic carbonates Behavior of homogeneous and heterogeneous catalysts in the oxidative carboxylation of olefins", Journal of Molecular Catalysis A: Chemical 182-183 (2002) 399-409.

Nomura, Ryoki, et al., "Synthesis of Cyclic Carbonates from Carbon Dioxide and Epoxides in the Presence of Organoantimony Compounds as Novel Catalysts", J. Org. Chsm. 1980,45, 3735-3738.

Kihara, Nobuhiro, et al., "Catalytic Activity of Various Salts in the Reaction of 2,3-Epoxypropyl Phenyl Ether and Carbon Dioxide under Atmospheric Pressure", J . Org. Chem. 1993,58, 6198-6202.

Kihara, Nobuhiro, et al., "Preparation of 1,3-Oxathiolane-2-thionebsy the Reaction of Oxirane and Carbon Disulfide", J. Org. Chem. 1996,60, 473-475.

Kruper, William J., et al., "Catalytic Formation of Cyclic Carbonates from Epoxides and C02 with Chromium Metalloporphyrinates", J. Org. Chem. 1996,60, 725-727.

Huntsman, "JEFFSOL Alkylene Carbonates" Copyright 2001.

Huntsman, Technical Bulletin, "JEFFSOL® Alkylene Carbonates Synthesis of Polycarbonates and 6-Membered Carbonates", JSPOLYCARB-0905 copyright 2005.

Clements, John H., "Reactive Applications of Cyclic Carbonates" , American Chemical Society, Received for Review Aug. 30, 2002—Revised Manuscript received Nov. 12, 2002—Accepted Nov. 13, 2002.

Huntsman, Technical Bulletin, "UltraPure® Ethylene Carbonate" , [CAS 96-49-1] 1124-1205 copyright 2005.

Taylor, Mark S., et al.: "Enantioselective Michael additions to a, β -unsaturated imides catalyzed by a Salen-Al complex," Sep. 2003 vol. 125 Issue 37, 11204-11205.

Xiao-Bing Ly, et al.: "Highly active eletrophile-nucleophile catalist system for the cycloadditions of C02 to epoxides at ambient temperature" Journal of Catalysts, Academic Press, Duluth MN, US, vol. 227, No. 2, Oct. 25, 2004 pp. 537-541, XP004583891 (cited in the application, scheme 1; table 1).

David A. Atwood, Melanie J. Harvey: "Group 13 Compounds incorporating Salen Ligands" Chem, Rev., vol. 101, 2001, pp. 37-52, XP002496197 (cited in the application; chapter "B", table 1).

Maroto-Valer, M. Mercedes, "Photochemical transformation of carbon dioxide", School of Chemical, Environmental and Mining Engineering (SChEME) Nottingham Fuel and Energy Centre (NFEC) 1995 and 2006.

(56) References Cited

OTHER PUBLICATIONS

Donald J. Darensbourg; Making Plastics from Carbon Dioxide: Salen Metal Complexes as Catalysts for the Production of Polycarbonates from Epoxides and CO2: Chemical Review: 2007, vol. 107, No. 6 pp. 2388-2410; American Chemical Society; Published on Web Apr. 21, 2007.

Donald J. Darensbourg, Paolo Bottarelli, Jeremy R. Andreatta; Inquiry into the Formation of Cyclic Carbonates during the (Salen)CrX Catalyzed CO2/Cyclohexene Oxide Copolymerization Process in the Presense of Ionic Initiators; Macromolecules; 2007, vol. 40, No. 21, pp. 7727-7729: American Chemical Society; Published on Web Sep. 18, 2007.

Charlotte K. Williams, CO2 as a feedstock in polymer synthesis, Imperial College London; Jul. 27, 2006.

"Variations of the Earths's surface temperature: year 1000 to year 2100". Temperatures Today 2100, IPCC Intergovernmental Panel of Climate Change; Jul. 27, 2006.

\* cited by examiner

ALUMINUM COMPLEXES AND THEIR USE IN THE SYNTHESIS OF CYCLIC CARBONATES

CROSS-REFERENCE TO RELATED APPLICATIONS

This application claims priority to International Application No. PCT/GB2010/000488, filed on Mar. 17, 2010, which claims priority to Great Britain Patent Application No. 0904654.1, filed Mar. 18, 2009, each of which is incorporated by reference in its entirety.

The present invention relates to aluminium(acen) and aluminium (salacen) complexes and their use as catalysts for synthesising cyclic carbonates from epoxides and carbon dioxide.

Cyclic carbonates are commercially important products currently manufactured on a multi-tonne scale for use as polar aprotic solvents, additives, antifoam agents for anti-freeze, plasticisers, and monomers for polymer synthesis (see Darensbourg, et al., *Coord. Chem. Rev.*, 153 (1996), 155-174; Coates, et al., *Angew. Chem. Int. Ed.*, 43 (2004), 6618-6639; Zevenhoven et al. *Cat. Today* 2006, 115, 73-79).

The synthesis of cyclic carbonates generally involves the reaction of epoxides with carbon dioxide, and hence could be used to sequester carbon dioxide, thus reducing the level of greenhouse gases in the atmosphere.

Catalysts for the synthesis of cyclic carbonates from epoxides and carbon dioxide are known in the art (see Darensbourg, et al., *Coord. Chem. Rev.*, 153 (1996), 155-174; Yoshida, et al., *Chem. Eur. J.*, 10 (2004), 2886-2893; Sun, et al., *J. Organomet. Chem.*, 690 (2005), 3490-3497) although these require elevated reaction temperatures and/or high pressures of carbon dioxide, the reaction often being conducted in supercritical carbon dioxide (see Lu, et al., *App. Cat. A*, 234 (2002), 25-33).

Ratzenhofer, et al., (*Angew. Chemie Int. Ed. Engl.*, 19 (1980), 317-318) succeeded in carrying out the reaction between 2-methyloxirane and carbon dioxide at room temperature and atmospheric pressure using catalysts consisting of a mixture of a metal halide and a Lewis base. However, a long reaction time of 7 days was required. Kisch, et al., (*Chem. Ber.*, 119 (1986), 1090-1094), carrying out the same reaction under the same conditions and also using catalysts of this type, reports a reaction time of 3.5 to 93 hours using up to 4 mol % of a $ZnCl_2$ catalyst and up to 16 mol % of a $(nButyl)_4NI$ catalyst.

Lu, et al., (*J. Mol. Cat. A*, 210 (2004), 31-34; *J. Cat.*, 227 (2004), 537-541) describe the use of tetradentate Schiff-base aluminium complexes in conjunction with a quaternary ammonium salt or polyether-KY complexes as catalyst systems for the reaction of various epoxides with carbon dioxide at room temperature and about 6 atmospheres.

Metal(salen) complexes, including aluminium(salen) complexes, are well-known in the art for their use as catalysts. Lu, et al., *App. Cat. A*, 234 (2002), 25-33, describes the use of a monomeric aluminium(salen) catalyst.

Also known in the art is the method of synthesising aluminium(salen) catalysts by treating a salen ligand with $Me_3Al$, $Et_3Al$, $Me_2AlCl$, $Me_2AlOTf$, $Et_2AlBr$ or $Et_2AlCl$ in a two-stage process (reviewed in Atwood and Harvey, *Chem. Rev.*, 2001, 101, 37-52).

The present inventor has previously found that, in the presence of a tetraalkylammonium halide cocatalyst, dimeric aluminium(salen) complexes are highly active catalysts for the reaction of epoxides with carbon dioxide to produce cyclic carbonates, and allow the reaction to be carried out at room temperature and atmospheric pressure, using short reaction times and commercially viable amounts of catalyst, as described in Melendez, J., et al., *Eur. J. Inorg Chem*, 2007, 3323-3326 and WO 2008/132474. In copending application PCT/GB2009/000624, the present inventor has also discovered that the cocatalyst can be combined into the catalyst molecule, and that the combined catalysts and co-catalyst can be immobilised on a solid support.

The present inventor has now found that it is possible to simplify the structure of the catalyst. The catalysts disclosed below have cheaper starting materials (e.g. acetylacetone), and the starting materials are more readily available.

Accordingly a first aspect of the invention provides a dimeric aluminium catalyst of formula I:

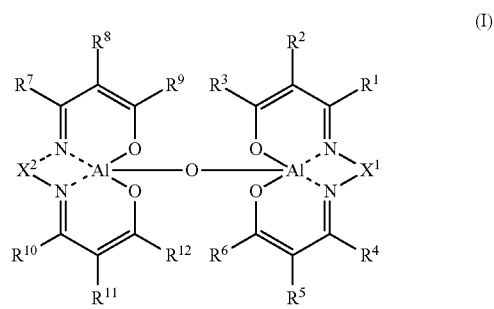

(I)

wherein:

a) each of the substituents $R^1$, $R^2$, $R^3$, $R^4$, $R^5$, $R^6$, $R^7$, $R^8$, $R^9$, $R^{10}$, $R^{11}$ and $R^{12}$, is independently selected from H, halo, optionally substituted $C_{1-20}$ alkyl (including $CAr_3$, where Ar is a $C_{5-20}$ aryl group), optionally substituted $C_{5-20}$ aryl, optionally substituted $C_{3-20}$ heterocyclyl, ether and nitro, where $R^2$, $R^5$, $R^8$ and $R^{11}$ may additionally be independently selected from optionally substituted ester or optionally substituted acyl or the pairs of $R^2$ and $R^3$, $R^5$ and $R^6$, $R^8$ and $R^9$ and $R^{11}$ and $R^{12}$ may independently together form a $C_{2-4}$ alkylene chain, optionally substituted by one or more groups selected from $C_{1-4}$ alkyl and $C_{5-7}$ aryl; or b) $R^5$ and $R^6$ together with the carbon atoms to which they are attached form an optionally substituted benzene ring of formula:

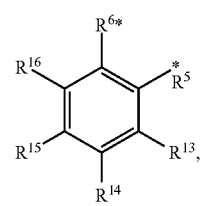

and $R^{11}$ and $R^{12}$ together with the carbon atoms to which they are attached form an optionally substituted benzene ring of formula:

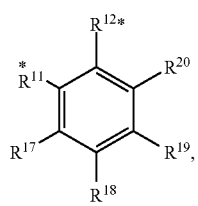

each of the substituents $R^1, R^2, R^3, R^4, R^7, R^8, R^9, R^{10}, R^{13}, R^{14}, R^{15}, R^{16}, R^{17}, R^{18}, R^{19}$ and $R^{20}$, is independently selected from H, halo, optionally substituted $C_{1-20}$ alkyl (including $CAr_3$, where Ar is a $C_{5-20}$ aryl group), optionally substituted $C_{5-20}$ aryl, optionally substituted $C_{3-20}$ heterocyclyl, ether and nitro;

$X^1$ and $X^2$ are independently either (i) a $C_{2-5}$ alkylene chain, which is optionally substituted by one or more groups selected from $C_{1-4}$ alkyl and $C_{5-7}$ aryl, or a $C_{1-3}$ bisoxyalkylene chain, which is optionally substituted by one or more groups selected from $C_{1-4}$ alkyl and $C_{5-7}$ aryl or (ii) represent a divalent group selected from $C_{5-7}$ arylene, $C_{9-10}$ arylene, bi-$C_{5-7}$ aryl, bi-$C_{9-10}$ aryl, $C_{5-7}$ cyclic alkylene and $C_{3-7}$ heterocyclylene, which may be optionally substituted.

In a second aspect, the present invention provides a catalyst defined in the first aspect of the invention, except that:

(i) (a) at least one of $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}$ and $R^{20}$ (where present) is selected from L-A, where L is a single bond or a $C_{1-10}$ alkylene group and A is an onium group paired with a counterion selected from Cl, Br and I; and/or (b) at least one of $X^1$ and $X^2$ is a divalent $C_{3-7}$ heterocyclene group, containing a ring atom which is a quaternary nitrogen forming part of an ammonium group paired with a counterion selected from Cl, Br and I; and/or (c) at least one of $X^1$ and $X^2$ is a $C_{2-5}$ alkylene chain or a $C_{1-3}$ bisoxyalkylene chain, substituted by a group -Q-L-A, where Q is either —C(=O)—O—, —C(=O)—NH—, or a single bond; and/or (d) at least one of $R^2, R^5, R^8$ and $R^{11}$ is -Q'-L-A, where Q' is either —C(=O)—O— or —C(=O)—;

and/or (ii) (a) one of $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}$ and $R^{20}$ (where present) is L-A', where L is as defined above and A' is an onium linking group bound to a solid support and paired with a counterion selected from Cl, Br and I; or (b) one of $X^1$ and $X^2$ is a divalent $C_{3-7}$ heterocyclene group, containing a ring atom which is a quaternary nitrogen forming part of an ammonium linking group bound to a solid support and paired with a counterion selected from Cl, Br and I; or (c) one of $X^1$ and $X^2$ is a $C_{2-5}$ alkylene chain or a $C_{1-3}$ bisoxyalkylene chain, substituted by a group -Q-L-A'; or (d) one of $R^2, R^5, R^8$ and $R^{11}$ is -Q'-L-A'.

Thus, in catalysts of the second aspect, when the catalyst is covalently bound to a solid support, only one linking group to the solid support is present. However, one or more ammonium groups/quaternary nitrogen atoms may be present.

The catalysts of the first aspect or the second aspect where: (a) at least one of $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}$ and $R^{20}$ (where present) is selected from L-A; and/or (b) at least one of $X^1$ and $X^2$ is a divalent $C_{3-7}$ heterocyclene group, containing a ring atom which is a quaternary nitrogen atom forming part of an ammonium group; and/or (c) at least one of $X^1$ and $X^2$ is a $C_{2-5}$ alkylene chain or a $C_{1-3}$ bisoxyalkylene chain, substituted by a group -Q-L-A, where Q is either —C(=O)—O—, —C(=O)—, NH or a single bond and/or (d) at least one of $R^2, R^5, R^8$ and $R^{11}$ is -Q'-L-A, where Q' is either —C(=O)—O— or —C(=O)—, may be immobilized on a solid support, either by the use of steric effects or by electrostatic binding.

If the catalyst of the first or second aspects includes one or more chiral centres, then it may be a (wholly or partially) racemic mixture or other mixture thereof, for example, a mixture enriched in one enantiomer or diastereoisomer, a single enantiomer or diastereoisomer, or a mixture of the stereoisomers. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner. Preferably the catalyst of the first and second aspects is a single enantiomer, if a chiral centre is present.

In some embodiments, it is preferred that the catalysts are symmetrical, i.e. that the two aluminium ligands are the same. Therefore, it may be preferred that $X^1=X^2$, $R^1=R^7$, $R^2=R^8$, $R^3=R^9$, $R^4=R^{10}$, $R^5=R^{11}$, $R^6=R^{12}$ and (if present) $R^{13}=R^{17}$, $R^{14}=R^{18}$, $R^{15}=R^{19}$ and $R^{16}=R^{20}$.

A third aspect of the present invention provides a process for the production of cyclic carbonates comprising contacting an epoxide with carbon dioxide in the presence of a dimeric aluminium(acen) or aluminium(salacen) catalyst according to the first aspect of the invention in combination with a co-catalyst capable of supplying $Y^-$, where Y is selected from Cl, Br and I; or in the presence of a dimeric aluminium(acen) or aluminium(salacen) catalyst according to the second aspect of the invention.

The cocatalyst is preferably soluble in the reaction mixture. Suitable sources of $Y^-$ are MY, where M is a suitable cation, such as onium halides, which include, but are not limited to, $R_4NY, R_3SY, R_4PY$ and $R_4SbY$, where each R is independently selected from optionally substituted $C_{1-10}$ alkyl, $C_{3-20}$ heterocyclyl and $C_{5-20}$ aryl groups and one R can be an acyl group, and simple halides, e.g. NaCl, KI.

The reaction of the third aspect may be defined as follows:

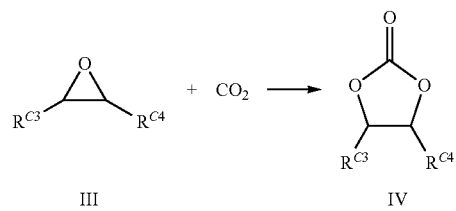

wherein $R^{C3}$ and $R^{C4}$ are independently selected from H, optionally substituted $C_{1-10}$ alkyl, optionally substituted $C_{3-20}$ heterocyclyl and optionally substituted $C_{5-20}$ aryl, or $R^{C3}$ and $R^{C4}$ form an optionally substituted linking group between the two carbon atoms to which they are respectively attached. The linking group, together with the carbon atoms to which it is attached, may form an optionally substituted $C_{5-20}$ cycloalkyl or $C_{5-20}$ heterocyclyl group. The $C_{5-20}$ cycloalkyl or $C_{5-20}$ heterocyclyl group may be substituted only in a single position on the ring, for example, adjacent the epoxide. Suitable substituents, include optionally substituted $C_{1-10}$ alkyl, optionally substituted $C_{3-20}$ heterocyclyl and optionally substituted $C_{5-20}$ aryl.

A possible substituent for the $C_{1-10}$ alkyl group is a $C_{5-20}$ aryl group.

The third aspect of the invention also provides the use of a dimeric aluminium(acen) or aluminium (salacen)) catalyst of the first aspect of the invention in combination with a co-catalyst capable of supplying Y⁻, or a dimeric aluminium (acen) or aluminium(salacen) catalyst of the second aspect of the invention for the production of cyclic carbonates from epoxides.

A fourth aspect of the invention provides a process for the synthesis of a dimeric aluminium(acen) or aluminium(salacen) catalyst of formula I according to the first or second aspects of the invention.

DETAILED DESCRIPTION OF THE INVENTION

Definitions

Epoxide: The term "epoxide", as used herein, may pertain to a compound of the formula:

wherein $R^{C3}$ and $R^{C4}$ are independently selected from H, optionally substituted $C_{1-10}$ alkyl, optionally substituted $C_{3-20}$ heterocyclyl and optionally substituted $C_{5-20}$ aryl, or $R^{C3}$ and $R^{C4}$ form an optionally substituted linking group between the two carbon atoms to which they are respectively attached. The linking group, together with the carbon atoms to which it is attached, may form an optionally substituted $C_{5-20}$ cycloalkyl or $C_{5-20}$ heterocylyl group. The $C_{5-20}$ cycloalkyl or $C_{5-20}$ heterocylyl group may be substituted only in a single position on the ring, for example, adjacent the epoxide. Suitable substituents, include optionally substituted $C_{1-10}$ alkyl, optionally substituted $C_{3-20}$ heterocyclyl and optionally substituted $C_{5-20}$ aryl.

The optional substituents may be selected from: $C_{1-10}$ alkyl, $C_{3-20}$ heterocyclyl, $C_{5-20}$ aryl, halo, hydroxy, ether, cyano, nitro, carboxy, ester, amido, amino, acylamido, ureido, acyloxy, thiol, thioether, sulfoxide, sulfonyl, thioamido and sulfonamino.

In some embodiments, the $C_{1-10}$ alkyl group is substituted by a $C_{5-20}$ aryl group.

Preferably, the epoxide is a terminal epoxide, i.e. $R^{C4}$=H.

In some embodiments, $R^{C3}$ is selected from optionally substituted $C_{1-4}$ alkyl and optionally substituted $C_{5-7}$ aryl. In some of these embodiments $R^{C3}$ is unsubstituted.

Preferred epoxides are ethylene oxide ($R^{C3}=R^{C4}$=H), propylene oxide ($R^{C3}$=methyl, $R^{C4}$=H) butylene oxide ($R^{C3}$=ethyl, $R^{C4}$=H), and styrene oxide ($R^{C3}$=phenyl, $R^{C4}$=H).

Cyclic carbonate: the term "cyclic carbonate", as used herein, may pertain to a compound of the formula:

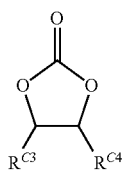

wherein $R^{C3}$ and $R^{C4}$ are as defined above.

Solid support: Catalysts of the present invention may be immobilized on a solid support by:
(a) covalent binding (those where one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ (if present) is selected from L-A' or one of $X^1$ and $X^2$ contains a quaternary nitrogen forming part of an ammonium linking group);
(b) steric trapping; or
(c) electrostatic binding.

These various methods are reviewed by Carlos Baleizão and Hermenegildo Garcia in "Chiral Salen Complexes: An Overview to Recoverable and Reusable Homogeneous and Heterogeneous Catalysts" (*Chem. Rev.* 2006, 106, 3987-4043).

For covalent binding, the solid support needs to contain or be derivatized to contain reactive functionalities which can serve for covalently linking a compound to the surface thereof. Such materials are well known in the art and include, by way of example, silicon dioxide supports containing reactive Si—OH groups, polyacrylamide supports, polystyrene supports, polyethyleneglycol supports, and the like. A further example is sol-gel materials. Silica can be modified to include a 3-chloropropyloxy group by treatment with (3-chloropropyl)triethoxysilane. Another example is Al pillared clay, which can also be modified to include a 3-chloropropyloxy group by treatment with (3-chloropropyl)triethoxysilane. Such supports will preferably take the form of small beads, pins/crowns, laminar surfaces, pellets or disks. They may also take the form of powders. Solid supports for covalent binding of particular interest in the present invention include siliceous MCM-41 and MCM-48 (modified with 3-chloropropyl groups), ITQ-2 and amorphous silica, SBA-15 and hexagonal mesoporous silica. Also of particular interest are sol-gels. Other conventional forms may also be used.

For steric trapping, the most suitable class of solid support is zeolites, which may be natural or modified. The pore size must be sufficiently small to trap the catalyst but sufficiently large to allow the passage of reactants and products to and from the catalyst. Suitable zeolites include zeolites X, Y and EMT as well as those which have been partially degraded to provide mesopores, that allow easier transport of reactants and products.

For the electrostatic binding of the catalyst to a solid support, typical solid supports may include silica, Indian clay, Al-pillared clay, Al-MCM-41, K10, laponite, bentonite, and zinc-aluminium layered double hydroxide. Of these silica and montmorillonite clay are of particular interest.

Alkyl: The term "alkyl", as used herein, pertains to a monovalent moiety obtained by removing a hydrogen atom from a carbon atom of a hydrocarbon having from 1 to 20 carbon atoms (unless otherwise specified), which may be aliphatic or alicyclic and which may be saturated or unsaturated (e.g. partially saturated, fully unsaturated). Thus, the term "alkyl" includes the sub-classes alkenyl, alkynyl, cycloalkyl, cycloalkenyl, cycloalkynyl, etc., as discussed below.

Alkylene: The term "alkylene", as used herein, pertains to a divalent moiety obtained by removing two hydrogen atoms from one or two carbon atoms of a hydrocarbon having from 1 to 20 carbon atoms (unless otherwise specified), which may be aliphatic or alicyclic and which may be saturated or unsaturated (e.g. partially saturated, fully unsaturated). Thus, the term "alkylene" includes the sub-classes alkenylene, alkynylene, cycloalkylene, cycloalkenylene, cycloalkynylene, etc., as discussed below.

In the context of alkyl and alkylene groups, the prefixes (e.g. $C_{1-4}$, $C_{1-7}$, $C_{1-20}$, $C_{2-7}$, $C_{3-7}$, etc.) denote the number of carbon atoms, or the range of number of carbon atoms. For example, the term "$C_{1-4}$ alkyl", as used herein, pertains to an alkyl group having from 1 to 4 carbon atoms. Examples of groups of alkyl groups include $C_{1-4}$ alkyl ("lower alkyl"), $C_{1-7}$ alkyl and $C_{1-20}$ alkyl. Note that the first prefix may vary according to other limitations; for example, for unsaturated alkyl groups, the first prefix must be at least 2; for cyclic alkyl groups, the first prefix must be at least 3; etc. For example, the term "$C_{1-7}$ alkylene", as used herein, pertains to an alkylene group having from 1 to 7 carbon atoms.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), and heptyl ($C_7$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Examples of (unsubstituted) saturated alkylene groups include, but are not limited to, methylene ($C_1$), ethylene ($C_2$), propylene ($C_3$), butylene ($C_4$), pentylene ($C_5$), hexylene ($C_6$), and heptylene ($C_7$).

Examples of (unsubstituted) saturated linear alkylene groups include, but are not limited to, methylene ($C_1$), ethylene ($C_2$), n-propylene ($C_3$), n-butylene ($C_4$), n-pentylene (amylene) ($C_5$), n-hexylene ($C_6$), and n-heptylene ($C_7$).

Examples of (unsubstituted) saturated branched alkyl groups include iso-propylene ($C_3$), iso-butylene ($C_4$), sec-butylene ($C_4$), tert-butylene ($C_4$), iso-pentylene ($C_5$), and neo-pentylene ($C_5$).

Alkenyl: The term "alkenyl", as used herein, pertains to an alkyl group having one or more carbon-carbon double bonds. Examples of groups of alkenyl groups include $C_{2-4}$ alkenyl, $C_{2-7}$ alkenyl, $C_{2-20}$ alkenyl.

Examples of (unsubstituted) unsaturated alkenyl groups include, but are not limited to, ethenyl (vinyl, —CH=CH$_2$), 1-propenyl (—CH=CH—CH$_3$), 2-propenyl (allyl, —CH$_2$—CH=CH$_2$), isopropenyl (1-methylvinyl, —C(CH$_3$)=CH$_2$), butenyl ($C_4$), pentenyl ($C_5$), and hexenyl ($C_6$).

Alkenylene: The term "alkenylene", as used herein, pertains to an alkylene group having one or more carbon-carbon double bonds. Examples of groups of alkenylene groups include $C_{2-4}$ alkenylene, $C_{2-7}$ alkenylene, $C_{2-20}$ alkenylene.

Alkynyl: The term "alkynyl", as used herein, pertains to an alkyl group having one or more carbon-carbon triple bonds. Examples of groups of alkynyl groups include $C_{2-4}$ alkynyl, $C_{2-7}$ alkynyl, $C_{2-20}$ alkynyl.

Examples of (unsubstituted) unsaturated alkynyl groups include, but are not limited to, ethynyl (ethinyl, —C≡CH) and 2-propynyl (propargyl, —CH$_2$—C≡CH).

Alkynylene: The term "alkynyl", as used herein, pertains to an alkylene group having one or more carbon-carbon triple bonds. Examples of groups of alkynylene groups include $C_{2-4}$ alkynylene, $C_{2-7}$ alkynylene, $C_{2-20}$ alkynylene.

Cycloalkyl: the term "cycloalkyl", as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g. partially unsaturated, fully unsaturated), which moiety has from 3-20 carbon atoms (unless otherwise specified), including from 3 to 20 ring atoms. Thus, the term "cycloalkyl" includes the sub-classes cycloalkenyl and cycloalkynyl. Preferably, each ring has from 3 to 7 ring atoms. Examples of groups of cycloalkyl groups include $C_{3-20}$ cycloalkyl, $C_{3-15}$ cycloalkyl, $C_{3-10}$ cycloalkyl, $C_{3-7}$ cycloalkyl.

Cycloalkylene: the term "cycloalkylene", as used herein, pertains to an alkylene group which is also a cyclyl group; that is, a divalent moiety obtained by removing two hydrogen atoms from one or two alicyclic ring atoms of a carbocyclic ring of a carbocyclic compound, which carbocyclic ring may be saturated or unsaturated (e.g. partially unsaturated, fully unsaturated), which moiety has from 3-20 carbon atoms (unless otherwise specified), including from 3 to 20 ring atoms. Thus, the term "cycloalkylene" includes the sub-classes cycloalkenylene and cycloalkynylene. Preferably, each ring has from 3 to 7 ring atoms. Examples of groups of cycloalkylene groups include $C_{3-20}$ cycloalkylene, $C_{3-15}$ cycloalkylene, $C_{3-10}$ cycloalkylene, $C_{3-7}$ cycloalkylene.

Cyclic alkylene: The term "cyclic alkylene" as used herein pertains to a divalent moiety obtained by removing a hydrogen atom from each of two adjacent alicyclic ring atoms of a carbocyclic ring of a carbocyclic compound, which carbocyclic ring may be saturated or unsaturated (e.g. partially saturated, fully unsaturated), which moiety has from 3 to 20 carbon atoms (unless otherwise specified), including from 3 to 20 ring atoms. Preferably each ring has from 5 to 7 ring atoms. Examples of groups of cyclic alkylene groups include $C_{3-20}$ cyclic alkylenes, $C_{3-15}$ cyclic alkylenes, $C_{3-10}$ cyclic alkylenes, $C_{3-7}$ cyclic alkylenes.

Examples of cycloalkyl groups and cyclic alkylene groups include, but are not limited to, those derived from:

saturated monocyclic hydrocarbon compounds: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds: thujane ($C_{10}$), carane ($C_{10}$), pinane ($C_{10}$), bornane ($C_7$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds: camphene ($C_{10}$), limonene ($C_{10}$), pinene ($C_{10}$);

polycyclic hydrocarbon compounds having an aromatic ring:
indene ($C_9$), indane (e.g., 2,3-dihydro-1H-indene) ($C_9$), tetralin (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Heterocyclyl: The term "heterocyclyl", as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

Heterocyclylene: The term "heterocyclylene", as used herein, pertains to a divalent moiety obtained by removing a hydrogen atom from each of two adjacent ring atoms of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

The heterocyclyl or heterocyclylene group may be bonded via carbon or hetero ring atoms. Preferably, the heterocyclylene group is bonded via two carbon atoms.

When referring to heterocyclyl or heterocyclylene groups, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$ heterocyclyl", as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Similarly, the term "$C_{5-6}$ heterocyclylene", as used herein, pertains to a heterocyclylene group having 5 or 6 ring atoms. Examples of groups of heterocyclylene groups include $C_{3-20}$ heterocyclylene, $C_{5-20}$ heterocyclylene, $C_{3-15}$ heterocyclylene, $C_{5-15}$ heterocyclylene, $C_{3-12}$ heterocyclylene, $C_{5-12}$ heterocyclylene, $C_{3-10}$ heterocyclylene, $C_{5-10}$ heterocyclylene, $C_{3-7}$ heterocyclylene, $C_{5-7}$ heterocyclylene, and $C_{5-6}$ heterocyclylene.

Examples of monocyclic heterocyclyl and heterocyclylene groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl and heterocyclylene groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 carbon atoms.

The ring atoms may be all carbon atoms, as in "carboaryl groups" in which case the group may conveniently be referred to as a "$C_{5-20}$ carboaryl" group.

$C_{5-20}$ arylene: The term "$C_{5-20}$ arylene", as used herein, pertains to a divalent moiety obtained by removing a hydrogen atom from each of two adjacent ring atoms of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 carbon atoms.

The ring atoms may be all carbon atoms, as in "carboarylene groups" in which case the group may conveniently be referred to as a "$C_{5-20}$ carboarylene" group.

Examples of $C_{5-20}$ aryl and $C_{5-20}$ arylene groups which do not have ring heteroatoms (i.e. $C_{5-20}$ carboaryl and $C_{5-20}$ carboarylene groups) include, but are not limited to, those derived from benzene (i.e. phenyl) ($C_6$), naphthalene ($C_{10}$), anthracene ($C_{14}$), phenanthrene ($C_{14}$), and pyrene ($C_{16}$).

Alternatively, the ring atoms may include one or more heteroatoms, including but not limited to oxygen, nitrogen, and sulfur, as in "heteroaryl groups" or "heteroarylene groups". In this case, the group may conveniently be referred to as a "$C_{5-20}$ heteroaryl" or "$C_{5-20}$ heteroarylene" group, wherein "$C_{5-20}$" denotes ring atoms, whether carbon atoms or heteroatoms. Preferably, each ring has from 5 to 7 ring atoms, of which from 0 to 4 are ring heteroatoms.

The heteroaryl or heteroarylene group may be bonded via carbon or hetero ring atoms. Preferably, the heteroarylene group is bonded via two carbon atoms.

Examples of $C_{5-20}$ heteroaryl and $C_{5-20}$ heteroarylene groups include, but are not limited to, $C_5$ heteroaryl and $C_5$ heteroarylene groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

Examples of $C_{5-20}$ heteroaryl and $C_{5-20}$ heteroarylene groups which comprise fused rings, include, but are not limited to, $C_9$ heteroaryl and $C_9$ heteroarylene groups derived from benzofuran, isobenzofuran, benzothiophene, indole, isoindole; $C_{10}$ heteroaryl and $C_{10}$ heteroarylene groups derived from quinoline, isoquinoline, benzodiazine, pyridopyridine; $C_{14}$ heteroaryl and $C_{14}$ heteroarylene groups derived from acridine and xanthene.

Bi-$C_{5-20}$ aryl: The term "bi-$C_{5-20}$ aryl", as used herein, pertains to a divalent moiety obtained by removing a hydrogen atom from two aromatic ring atoms of a bi-$C_{5-20}$ aromatic compound, said compound comprising two $C_{5-20}$ aromatic moieties joined by a single bond, each moiety having one ring, or two or more rings (e.g., fused), and having from 5 to 20 ring atoms, and wherein at least one of said ring(s) is an aromatic ring. Preferably, each ring has from 5 to 7 carbon atoms.

The ring atoms may be all carbon atoms, as in "carboaryl groups" in which case the group may conveniently be referred to as a "$C_{5-20}$ carboaryl" group. Examples of bi-$C_{5-20}$ aryl groups which do not have ring heteroatoms (i.e. bi-$C_{5-20}$ carboaryl) include, but are not limited to, those where both moieties are derived from benzene (i.e. bi-phenyl)($C_6$), naphthalene (i.e. bi-naphyhyl)($C_{10}$), anthracene ($C_{14}$), phenanthrene ($C_{14}$), and pyrene ($C_{16}$).

Alternatively, the ring atoms of one or both moieties may include one or more heteroatoms, including but not limited to oxygen, nitrogen, and sulfur, as in "heteroaryl groups" or "heteroarylene groups". In this case, the group may conveniently be referred to as a "bi-$C_{5-20}$ heteroaryl" group if both moieties contain ring heteroatoms or a "bi-$C_{5-20}$ carboaryl-$C_{5-20}$ heteroaryl" group if only one moiety comprises a ring heteroatom. "$C_{5-20}$" denotes ring atoms, whether carbon atoms or heteroatoms. Preferably, each ring has from 5 to 7 ring atoms, of which from 0 to 4 are ring heteroatoms.

A "bi-$C_{5-7}$ aryl" group is one where both moieties are $C_{5-7}$ aryl groups. Likewise, a "bi-$C_{9-10}$ aryl" group is one where both moieties are $C_{9-10}$ aryl groups Bisoxy-$C_{1-3}$ alkylene: —O—$(CH_2)_m$—O—, where m is 1 to 3.

The above alkyl, alkylene, bisoxyalkylene, cyclic alkylene, heterocyclyl, heterocyclylene, aryl, bi-aryl and arylene groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —$NO_2$.

Cyano (nitrile, carbonitrile): —CN.

Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl), —C(=O)C($CH_3)_3$ (pivaloyl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)O$CH_3$, —C(=O)O$CH_2CH_3$, —C(=O)OC($CH_3)_3$, and —C(=O)OPh.

Amido (carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(=O)$NH_2$, —C(=O)NH$CH_3$, —C(=O)N($CH_3)_2$, —C(=O)NH$CH_2CH_3$, and —C(=O)N($CH_2CH_3)_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinylcarbonyl.

Amino: —$NR^1R^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —$NH_2$, —NH$CH_3$, —NHCH($CH_3)_2$, —N($CH_3)_2$, —N($CH_2CH_3)_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. In particular, the cyclic amino groups may be substituted on their ring by any of the substituents defined here, for example carboxy, carboxylate and amido.

Onium group: —$NR_3$ (ammonium group), —$SR_2$, —$PR_3$ and —$SbR_3$, where each R is independently selected from optionally substituted $C_{1-10}$ alkyl, $C_{3-20}$ heterocyclyl and $C_{5-20}$ aryl groups and one R can be an acyl group and one or two R can be hydrogen. Two or three of the onium substituents may join together to form cyclic or cage-like structures.

Ammonium group: —$NR^{N1}R^{N2}R^{N3}$, wherein $R^{N1}$, $R^{N2}$ and $R^{N3}$ are independently ammonium substituents, for example, a $C_{1-7}$ alkyl group, a $C_{3-20}$ heterocyclyl group, or a $C_{5-20}$ aryl group and where one or two of $R^{N1}$, $R^{N2}$ and $R^{N3}$ may also be H. One of $R^{N1}$, $R^{N2}$ and $R^{N3}$ may be a $C_{1-3}$ alkoxy (—$(CH_2)_{1-3}$—OH) group. Two or three of the ammonium substituents may join together to form cyclic or cage-like structures. Examples of ammonium groups include, but are not limited to, —NH($CH_3)_2$, —NH(CH($CH_3)_2)_2$, —N($CH_3)_3$, —N($CH_2CH_3)_3$, and —$NH_2$Ph.

Onium linking group: —$NR_2R'$— (ammonium linking group), —$SRR'$—, —$PR_2R'$— and —$SbR_2R'$—, where each R is independently selected from optionally substituted $C_{1-10}$ alkyl, $C_{3-20}$ heterocyclyl and $C_{5-20}$ aryl groups and one R can be an acyl group and one or two R can be hydrogen. Two of the onium substituents may join together to form cyclic or cage-like structures. R' is a divalent onium substituent, for example, a $C_{1-7}$ alkylene group, a $C_{3-20}$ heterocyclylene group, or a $C_{5-20}$ arylene group or a divalent $C_{1-3}$ alkyloxylene (—$(CH_2)_{1-3}$—O—) group.

Ammonium linking group: —$NR^{N1}R^{N2}R^{N4}$—, wherein $R^{N1}$ and $R^{N2}$ are independently ammonium substituents, for example, a $C_{1-7}$ alkyl group, a $C_{3-20}$ heterocyclyl group, or a $C_{5-20}$ aryl group and where one or both of $R^{N1}$ and $R^{N2}$ may also be H. The two ammonium substituents may join together to form a cyclic structure. $R^{N4}$ is a divalent ammonium substituent, for example, a $C_{1-7}$ alkylene group, a $C_{3-20}$ heterocyclylene group, or a $C_{5-20}$ arylene group or a divalent $C_{1-3}$ alkyloxylene (—$(CH_2)_{1-3}$—O—) group. Examples of ammonium linking groups include, but are not limited to, —NH($CH_3$)($CH_2$)—, —NH(CH($CH_3)_2$)(C($CH_3)_2$)—, —N($CH_3)_2$($CH_2$)—, —N($CH_2CH_3)_2$($CH_2CH_2$)—, and —NHPh($CH_2$)—.

Acylamido (acylamino): —$NR^1C$(=O)$R^2$, wherein $R^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and $R^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)$CH_3$, —NHC(=O)$CH_2CH_3$, and —NHC(=O)Ph. $R^1$ and $R^2$ may together form a cyclic structure, as in, for example, succinimidyl, maleimidyl, and phthalimidyl:

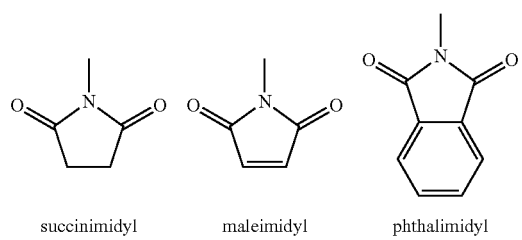

succinimidyl    maleimidyl    phthalimidyl

Ureido: —N($R^1$)CON$R^2R^3$ wherein $R^2$ and $R^3$ are independently amino substituents, as defined for amino groups, and $R^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCON$H_2$, —NHCONHMe, —NHCONHEt, —NHCONMe$_2$, —NH- CONEt$_2$, —NMeCONH$_2$, —NMeCONHMe, —NMeCON-HEt, —NMeCONMe$_2$, —NMeCONEt$_2$ and —NHCON-HPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, —OC(=O)C$_6$H$_4$F, and —OC(=O)CH$_2$Ph.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Sulfoxide (sulfinyl): —S(=O)R, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —S(=O)CH$_3$ and —S(=O)CH$_2$CH$_3$.

Sulfonyl (sulfone): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Sulfonamino: —NR$^1$S(=O)$_2$R, wherein R$^1$ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

As mentioned above, the groups that form the above listed substituent groups, e.g. $C_{1-7}$ alkyl, $C_{3-20}$ heterocyclyl and $C_{5-20}$ aryl, may themselves be substituted. Thus, the above definitions cover substituent groups which are substituted.

Chemically Protected Forms

It may be convenient or desirable to prepare, purify, handle and/or use the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

Unless otherwise specified, a reference to a particular compound also includes chemically protected forms thereof.

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O.).

For example, a carboxylic acid group may be protected as an ester for example, as: a $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$ alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

In particular application in the present invention is the protection of hydroxy and amino groups.

Catalysed Reactions

In one aspect of the present invention, there is provided a process for the production of cyclic carbonates comprising contacting an epoxide with carbon dioxide in the presence of a dimeric aluminium(acen) or aluminium(salacen) catalyst of formula I.

This reaction has the advantage that it may be carried out at easily accessible temperatures of between 0 and 40° C. and pressures of between 0.5 and 2 atm. The reaction may even be carried out at temperatures of between 0 and 140° C. and pressures of between 0.5 and 5 atm. Preferably, the reaction temperature lies between 20 and 30° C. Yields of over 50% may be achieved with short reaction times of 3 to 24 hours, using commercially viable amounts of catalyst, that is, from 0.1 to 10 mol %, preferably 0.1 to 2.5 mol %. In some cases, yields of over 70% or over 90% may be achieved under these conditions.

The reaction may also be carried out in a flow reactor, wherein the reaction is continuous.

In some embodiments, the carbon dioxide may be supplied heated, and in other embodiments, the reaction may be heated by a conventional or microwave system.

In particular embodiments of the invention, there is provided a dimeric aluminium catalyst of formula Ia:

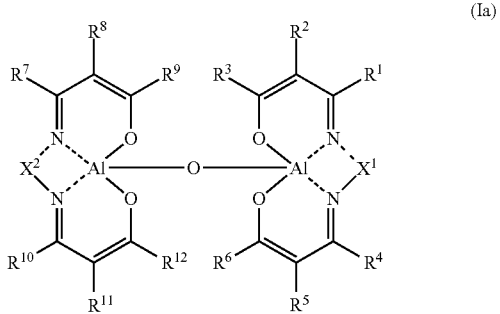

(Ia)

wherein:
a) each of the substituents $R^1$, $R^2$, $R^3$, $R^4$, $R^5$, $R^6$, $R^7$, $R^8$, $R^9$, $R^{10}$, $R^{11}$ and $R^{12}$, is independently selected from H, halo, optionally substituted $C_{1-20}$ alkyl (including $CAr_3$, where Ar is a $C_{5-20}$ aryl group), optionally substituted $C_{5-20}$ aryl, optionally substituted $C_{3-20}$ heterocyclyl, ether and nitro; or
b) $R^5$ and $R^6$ together with the carbon atoms to which they are attached form an optionally substituted benzene ring of formula:

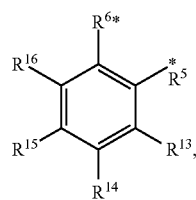

and
$R^{11}$ and $R^{12}$ together with the carbon atoms to which they are attached form an optionally substituted benzene ring of formula:

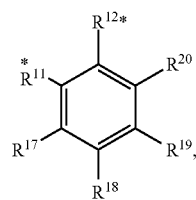

each of the substituents $R^1$, $R^2$, $R^3$, $R^4$, $R^7$, $R^8$, $R^9$, $R^{10}$, $R^{13}$, $R^{14}$, $R^{15}$, $R^{16}$, $R^{17}$, $R^{18}$, $R^{19}$ and $R^{20}$, is independently selected from H, halo, optionally substituted $C_{1-20}$ alkyl (including $CAr_3$, where Ar is a $C_{5-20}$ aryl group), optionally substituted $C_{5-20}$ aryl, optionally substituted $C_{3-20}$ heterocyclyl, ether and nitro;

$X^1$ and $X^2$ are independently either (i) a $C_{2-5}$ alkylene chain, which is optionally substituted by one or more groups selected from $C_{1-4}$ alkyl and $C_{5-7}$ aryl, or a $C_{1-3}$ bisoxyalkylene chain, which is optionally substituted by one or more groups selected from $C_{1-4}$ alkyl and $C_{5-7}$ aryl or (ii) represent a divalent group selected from $C_{5-7}$ arylene, $C_{9-10}$ arylene, bi-$C_{5-7}$ aryl, bi-$C_{9-10}$ aryl, $C_{5-7}$ cyclic alkylene and $C_{3-7}$ heterocyclylene, which may be optionally substituted.

In particular embodiments of the invention, there is provided a catalyst of formula (Ia) as defined above, except that:
(i) (a) at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ (where present) is selected from L-A, where L is a single bond or a $C_{1-10}$ alkylene group and A is an onium group paired with a counterion selected from Cl, Br and I; and/or
(b) at least one of $X^1$ and $X^2$ is a divalent $C_{3-7}$ heterocyclene group, containing a ring atom which is a quaternary nitrogen forming part of an ammonium group paired with a counterion selected from Cl, Br and I; and/or
(c) at least one of $X^1$ and $X^2$ is a $C_{2-5}$ alkylene chain or a $C_{1-3}$ bisoxyalkylene chain, substituted by a group -Q-L-A, where Q is either —C(=O)—O—, —C(=O)—NH—, or a single bond;
and/or
(ii) (a) one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ (where present) is L-A', where L is as defined above and A' is an onium linking group bound to a solid support and paired with a counterion selected from Cl, Br and I; or
(b) one of $X^1$ and $X^2$ is a divalent $C_{3-7}$ heterocyclene group, containing a ring atom which is a quaternary nitrogen forming part of an ammonium linking group bound to a solid support and paired with a counterion selected from Cl, Br and I; or
(c) one of $X^1$ and $X^2$ is a $C_{2-5}$ alkylene chain or a $C_{1-3}$ bisoxyalkylene chain, substituted by a group -Q-L-A'.

In some aspects of the invention, L is selected from a single bond and $C_{1-7}$ alkylene.

In some embodiments of the invention, the aluminium (acen) or aluminium (salacen) catalyst of formula I or Ia is symmetrical, such that $X^1=X^2$, $R^1=R^7$, $R^2=R^8$, $R^3=R^9$, $R^4=R^{10}$, $R^5=R^{11}$, $R^6=R^{12}$ and (if present) $R^{13}=R^{17}$, $R^{14}=R^{18}$, $R^{15}=R^{19}$ and $R^{16}=R^{20}$. In some embodiments, it is preferred that $R^1$, $R^4$, $R^7$, and $R^{19}$ are identical, $R^2$, $R^5$, $R^8$ and $R^{11}$ are identical, and $R^3$, $R^6$, $R^9$, and $R^{12}$ are identical.

In the embodiments of the invention where the aluminium (acen) or aluminium (salacen) catalyst of formula I is symmetrical then the alkylene group formed by $R^2$ and $R^3$ will be identical to that formed by $R^8$ and $R^9$, and the alkylene group formed by $R^5$ and $R^6$ will be identical to that formed by $R^{11}$ and $R^{12}$, if these groups are present.

If the catalyst is covalently bound to a solid support, then it will not be fully symmetrical.

In some embodiments, $X^1$ and $X^2$ are the same.

In some embodiments, $X^1$ and $X^2$ are independently selected from a $C_{2-5}$ alkylene chain, which is preferably unsubstituted, and a $C_{1-3}$ bisoxylakylene chain, which is preferably unsubstituted. These groups can be represented as —$(CH_2)_n$— or —O—$(CH_2)_p$—O—, where n is 2, 3, 4, or 5 and p is 1, 2, or 3. In these embodiments, n is preferably 2 or 3 and p is preferably 1 or 2. n is more preferably 2. In these embodiments $X^1$ and $X^2$ are preferably selected from —$(CH_2)_n$— (e.g. —$C_2H_4$—).

In other embodiments, $X^1$ and $X^2$ independently represent a divalent group selected from $C_{5-7}$ arylene, $C_{9-10}$ arylene, bi-$C_{5-7}$ aryl, bi-$C_{3-10}$ aryl, $C_{5-7}$ cyclic alkylene and $C_{3-7}$ heterocyclylene, which may be optionally substituted. Preferably $X^1$ and $X^2$ independently represent $C_{5-7}$ cyclic alkylene, and more preferably $C_6$ cyclic alkylene. This group is preferably saturated, and therefore is the group:

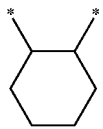

In other preferred embodiments, $X^1$ and $X^2$ independently represent $C_{5-7}$ heterocyclene, and more preferably $C_5$ heterocyclene. One such preferred group is:

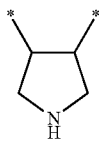

In this group, the nitrogen atom may be substituted, for example, by a $C_{1-4}$ alkyl group (e.g. methyl) that may itself be substituted, for example, by a $C_{3-7}$ aryl group (e.g. phenyl). Therefore a preferred group for $X^1$ and $X^2$ is:

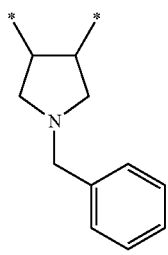 [SMILES: *C1CN(Cc2ccccc2)CC1*]

In other preferred embodiments, $X^1$ and $X^2$ independently represent $C_{5-7}$ arylene, which is more preferably $C_6$ arylene, and in particular, benzylene:

When $X^1$ and $X^2$ independently represent a divalent group selected from $C_{5-7}$ arylene, $C_{9-10}$ arylene, bi-$C_{5-7}$ aryl, bi-$C_{9-10}$ aryl, $C_{5-7}$ cyclic alkylene and $C_{3-7}$ heterocyclylene, they may preferably be unsubstituted. If they are substituted, then the substituents may be selected from nitro, halo, $C_{1-4}$ alkyl, including substituted $C_{1-4}$ alkyl, (e.g. methyl, benzyl), $C_{1-4}$ alkoxy (e.g. methoxy) and hydroxy.

In some embodiments, $R^5$ and $R^6$, and $R^{11}$ and $R^{12}$ do not form fused benzene rings.

In some embodiments, $R^1=R^4=R^7=R^{10}=H$.
In some embodiments, $R^3=R^6=R^9=R^{12}=H$.
In some embodiments, $R^1=R^4=R^7=R^{10}=Me$.
In some embodiments, $R^3=R^6=R^9=R^{12}=Me$.
In some embodiments, $R^2=R^5=R^8=R^{11}=H$.

In particularly preferred embodiments of the present invention, $R^1=R^4=R^7=R^{10}=Me$; $R^3=R^6=R^9=R^{12}=Me$; and $R^2=R^5=R^8=R^{11}=H$.

In some embodiments, $R^1=R^7=H$.
In some embodiments, $R^2=R^8=H$.
In some embodiments, $R^3=R^9=H$.
In some embodiments, $R^4=R^{10}=H$.
In some embodiments, $R^5$ and $R^6$ together with the atoms to which they are joined form a benzene ring, which is preferably unsubstituted.

In some embodiments, $R^{11}$ and $R^{12}$ together with the atoms to which they are joined form a benzene ring, which is preferably unsubstituted.

In particularly preferred embodiments of the present invention, $R^1=R^7=H$; $R^2=R^8=H$; $R^3=R^9=H$; $R^4=R^{10}=H$; $R^5$ and $R^6$ together with the atoms to which they are joined form an unsubstituted benzene ring; and $R^{11}$ and $R^{12}$ together with the atoms to which they are joined form an unsubstituted benzene ring.

If $R^2$, $R^5$, $R^8$ and $R^9$ are selected from optionally substituted ester or optionally substituted acyl, the ester group may be an unsubstituted $C_{1-7}$ alkyl ester, more preferably an unsubstituted $C_{1-4}$ alkyl ester (e.g. ethyl ester), and the acyl group may be an unsubstituted $C_{1-7}$ alkylacyl, more preferably an unsubstituted $C_{1-4}$ alkylacyl (e.g. methyl acyl).

In further embodiments of the invention, $R^2=R^5=R^8=R^{11}=$—$CO_2Me$. In these embodiments, it may be preferred that $R^1=R^4=R^7=R^{10}=H$, and $R^3=R^6=R^9=R^{12}=Me$. It may also or alternatively be preferred that $X^1$ and $X^2$ are —$C_2H_4$— or:

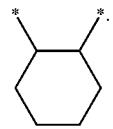

If a pair of $R^2$ and $R^3$, $R^5$ and $R^6$, $R^8$ and $R^9$ and $R^{11}$ and $R^{12}$ together form a $C_{2-4}$ alkylene chain, the chain may be unsubstituted.

In some embodiments, it is one or more of $R^2$, $R^5$, $R^8$ and $R^{11}$ that is -L-A or L-A'. In some of these embodiments, if one of these groups is -L-A', the other groups are -L-A. Alternatively, the other groups may be -L-$A^M$, where $A^M$ is a tertiary amine group, i.e. an amino group where the amino substituents are both not hydrogen, for example, $C_{1-7}$ alkyl (ethyl). The L in all these groups may be the same. In some further embodiments, one of $R^2$, $R^5$, $R^8$ and $R^{11}$ is -Q'-L-A or -Q'-L-A'. In some of these further embodiments, if one of these groups is -Q'-L-A', the other groups are -Q'-L-A. Alternatively, the other groups may be -Q'-L-$A^M$, where $A^M$ is a tertiary amine group, i.e. an amino group where the amino substituents are both not hydrogen, for example, $C_{1-7}$ alkyl (ethyl). The L in all these groups may be the same. In some embodiments, those of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ (where present) which do not comprise -L-A or -L-A' are independently selected (where appropriate) from H, $C_{1-7}$ alkyl, ether and nitro. If none of the groups are -L-A or -L-A' then they all may be independently selected (where appropriate) from H, $C_{1-7}$ alkyl, ether and nitro.

If a group selected from $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ (where present) is ether, then the ether group is preferably a $C_{1-7}$ alkoxy group and more preferably $C_{1-4}$ alkoxy group, e.g. methoxy.

If a group selected from $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ (where present) is $C_{1-7}$ alkyl, it may be $C_{1-4}$ alkyl, e.g. methyl, ethyl, propyl and butyl (preferably tert-butyl).

L is preferably unsubstituted.

L may preferably be a $C_{1-3}$ alkylene group, e.g. methylene, ethylene, propylene, and in some embodiments is methylene.

A may preferably be selected from ammonium groups, and in particular, those groups where $R^{N1}$, $R^{N2}$ and $R^{N3}$ are independently selected from $C_{1-7}$ alkyl groups and $C_{5-20}$ aryl groups, and where one or two of $R^{N1}$, $R^{N2}$ and $R^{N3}$ may also be H. Ammonium groups of particular interest in the present invention include, but are not limited to, —NH(CH$_3$)$_2$, —NH(CH(CH$_3$)$_2$)$_2$, —N(CH$_3$)$_3$, —N(CH$_2$CH$_3$)$_3$, and —NH$_2$Ph.

A' may preferably be selected from ammonium linking group, and in particular those groups where $R^{N1}$ and $R^{N2}$ are independently selected from $C_{1-7}$ alkyl groups and $C_{5-20}$ aryl groups, where one or both of $R^{N1}$ and $R^{N2}$ may also be H and where $R^{N4}$ is a $C_{1-7}$ alkylene group. Ammonium linking groups of particular interest in the present invention include, but are not limited to, —NH(CH$_3$)(CH$_2$)—, —NH(CH(CH$_3$)$_2$)(C(CH$_3$)$_2$)—, —N(CH$_3$)$_2$(CH$_2$)—, —N(CH$_2$CH$_3$)$_2$(CH$_2$CH$_2$)—, and —NHPh(CH$_2$)—.

In some embodiments, Q may be —C(=O)—O— or —C(=O)—NH—.

When X' and/or $X^2$ is substituted by -Q-L-A or -Q-L-A', it is preferably a $C_2$ or $C_3$ alkylene group, more preferably a $C_2$ alkylene group, and may be of the formula:

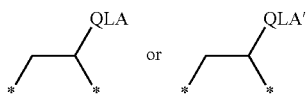

If $X^1$ or $X^2$ is a divalent $C_{3-7}$ heterocyclene group containing a ring atom which is a quaternary nitrogen atom, then it is preferably of the formula:

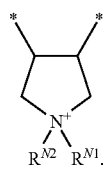

$R^{N1}$ and $R^{N2}$ in the above group are independently selected from $C_{1-7}$alkyl groups (including, for example, those substituted by a $C_6$ aryl group) and $C_{5-20}$ aryl groups, and where one of $R^{N1}$ and $R^{N2}$ may also be H. $R^{N1}$ and $R^{N2}$ groups of particular interest in above structure include, but are not limited to, —CH$_3$, —CH(CH$_3$)$_2$, and —CH$_2$Ph.

If $X^1$ or $X^2$ is a divalent $C_{3-7}$ heterocyclene group containing a ring atom which is a quaternary nitrogen forming part of an ammonium linking group, then it is preferably of the formula:

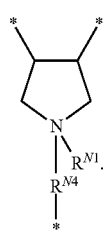

Compounds of particular interest are 6, 7, 10 and 11.

The reaction may be carried out under solvent-free conditions, depending on the epoxides used. In some cases, the epoxides or the cyclic carbonates may act as a solvent for the catalyst. In particular, the inventors have found that propylene carbonate acts a suitable reaction solvent.

Reactions using the catalyst of the first aspect, and some reactions using the catalyst of the second aspect, require the addition of a co-catalyst, $Y^-$, and in particular MY, where M is a suitable cation, such as onium halides, which include, but are not limited to, R$_4$NY, R$_3$SY, R$_4$PY and R$_4$SbY, where each R is independently selected from optionally substituted $C_{1-10}$ alkyl, $C_{3-20}$ heterocyclyl and $C_{5-20}$ aryl groups and one R can be an acyl group, and simple halides, e.g. NaCl, Kl.

It is preferred that the co-catalyst for this reaction is of the form R$_4$NY, where each R is independently $C_{1-10}$ alkyl and Y is selected from I, Br and Cl. R is preferably selected from $C_{3-5}$ alkyl, and more preferably is butyl. Y is preferably Br. Therefore, a particularly preferred co-catalyst is Bu$_4$NBr. The amount of co-catalyst is preferably less than 2.5%, more preferably less than 1.0 mol % and most preferably less than 0.5 mol %. In some embodiments using a catalyst of the second aspect of the invention, no separate co-catalyst is present.

The above preferences may be combined with each other in any way that is appropriate.

Manufacture of Dimeric Aluminium(Acen) and Aluminium (Salacen) Complexes

In a fourth aspect of the invention, there is provided a process for the production of dimeric aluminium(acen) and aluminium(salacen) catalysts of formula I.

When the catalyst of formula I comprises one or more onium group paired with a counterion, it may be synthesised from a precursor comprising the corresponding neutral groups (e.g. amine, sulphide, phosphine) by reaction with a organic halide (i.e. a $C_{1-7}$ alkyl, $C_{3-20}$ heterocyclyl or $C_{5-20}$ aryl halide), or an organic group with another leaving group (e.g. tosylate).

When the catalyst of formula I comprises an onium linking group bound to a solid support, it may be synthesised from a precursor catalyst comprising a corresponding neutral group (e.g. amine, sulphide, phosphine) by reaction with a halide derived solid support or a solid support derived with another leaving group (e.g. tosylate).

In catalysts where at least one of $R^2$, $R^5$, $R^8$ and $R^9$ are optionally substituted ester or optionally substituted acyl groups, the ligands may be synthesised from precursors of formulae:

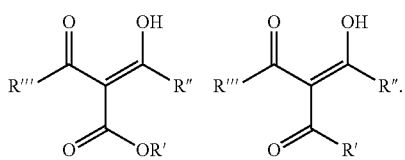

Such ligand synthesis is described, for example, in Yamada, et al., Bull. Chem. Soc. Jpn., 80(7) (2007), 1391-1401.

In catalysts where at least one of the pairs of $R^2$ and $R^3$, $R^5$ and $R^6$, $R^8$ and $R^9$ and $R^{11}$ and $R^{12}$ are independently together form a $C_{2-4}$ alkylene chain, optionally substituted by one or more groups selected from $C_{1-4}$ alkyl and $C_{5-7}$ aryl, or a $C_{1-3}$ bisoxyalkylene chain, which is optionally substituted by one or more groups selected from $C_{1-4}$ alkyl and $C_{5-7}$ aryl, the ligands may be synthesised from precursors of formulae:

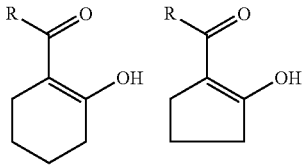

Such compounds are described, for example, in Barna and Robinson, *Tet Lett* 16 (1979), 1455-1458; Jones and Stokes, *Tet* 40(6) (1984), 1051-1060; Kuhakarn, et al., *Tet* 61 (2005), 8995-9000; Martins, et al., *J Het Chem*, 33 (1996), 1223-1231.

EXAMPLES

General Experimental Methods

IR Spectroscopy

IR spectra of liquids or of solids dissolved in a solvent were recorded between NaCl plates on a PE Spectrum 1 spectrometer. IR spectra of pure solids (ATR) were recorded on a Nicolet380 FTIR spectrometer fitted with a 'Smart orbit' attachment.

NMR

All NMR spectra were recorded at ambient temperature on a Bruker Avance 300 spectrometer. The sample was dissolved in $CDCl_3$ unless specified otherwise.

Mass Spectroscopy

GCMS were recorded on a Varian CP-800-SATURN 2200 GC/MS ion-trap mass spectrometer using a FactorFour (VF-5 ms) capillary column (30 m×0.25 mm) with helium as the carrier gas. The conditions used were: initial temperature 60° C., hold at initial temperature for 3 minutes then ramp rate 15° C./min to 270° C.; hold at final temperature for 5 minutes. For the first 3.50 minutes, the eluent was routed away from the mass detector. Subsequently, the detector was operated in full EI scan mode. Calibration was carried out by using a 50:50 mixture of pure isolated carbonate and reagent grade styrene oxide. Peak integration was found to be virtually 50% for each component.

Low and high resolution electrospray spectra were recorded on a Waters LCT

Premier mass spectrometer.

Synthesis of Key Intermediates

Acen Ligand (3)

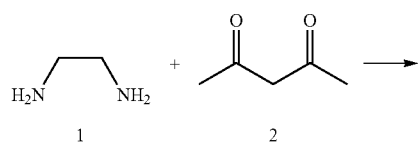

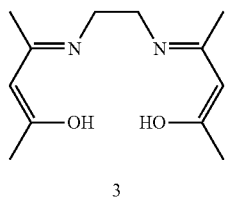

3

Prepared by the method of McCarthy, P. J., et al., *J. Am. Chem. Soc.*, 1955, 77, 5820. 1,2-Diaminoethane (1) (3.0 g, 3.3 mL, 49.9 mmol) was dissolved in ethanol (70 mL) and acetylacetone (2) (10.3 mL, 99.8 mmol) was added in a steady stream over a period of about 10 minutes whilst stirring the reaction mixture. The reaction was refluxed for 3 hours. After cooling, evaporation of the solvent in vacuo left a yellow solid which was purified by the addition of diethyl ether (ca. 100 mL). The desired ligand (3) (7.3 g, 32.4 mmol, 65%) was obtained as an off-white crystalline solid by suction filtration.

mp 116-118° C.

$\delta_H$(CDCl$_3$) 4.97 (2H, s), 3.4-3.3 (4H, m), 1.97 (6H, s), 1.88 (6H, s)

Salacen Ligand (5)

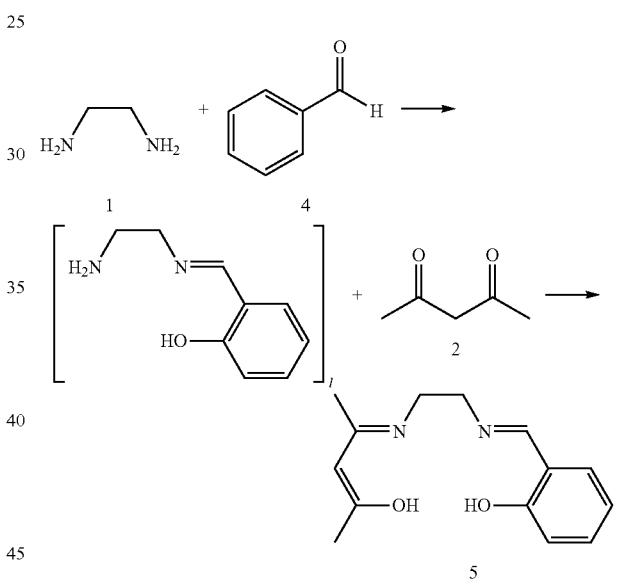

Preparation based on the method reported by Phan, N. T. S., et al., *Dalton Trans.*, 2004, 1348. Ethylene diamine (1) (2.7 g, 45.0 mmol) was dissolved in dichloromethane (50 mL) and salicylaldehyde (4) (5.0 g, 41.0 mmol) was added in a slow stream while stirring the reaction. The resulting yellow mixture was stirred at ambient temperature for a further 30 minutes. Acetyl acetone (2) (4.5 g, 45.0 mmol) was then added and the reaction mixture heated to reflux with stirring for one hour. The reaction was then allowed to cool to room temperature and was stirred overnight. Evaporation of the solvent gave a yellow solid which was taken up in the minimum volume of hot methanol required to dissolve all the solids (ca. 10 mL) and then cooled. A yellow crystalline precipitate formed which was filtered and identified as salen. The mother liquor was evaporated under vacuum to give the desired ligand (5) as a yellow/amber powder (2.7 g, 11.0 mmol, 27%).

Mp 122-126° C.

$\delta_H$(CDCl$_3$) 8.35 (1H, s), 7.3-7.2 (2H, m), 7.0-6.9 (2H, m), 4.93 (1H, s), 3.75 (2H, m), 3.41 (2H, m), 1.99 (3H, s), 1.96 (3H, s).

Pyrrolidine-Based Diamine Acen Ligand (9)

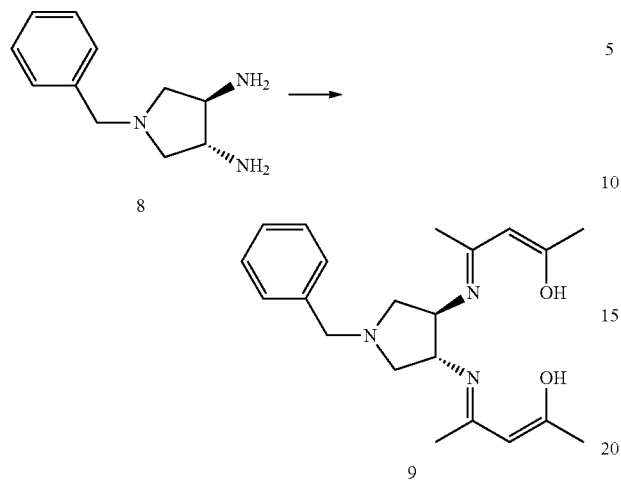

Diamine 8 was prepared by the literature method (Hato, Y.; Kano, T.; Maruoka, K. *Tetrahedron Letters*, 2006, 8467) from the precursor diazido species by hydrogenation (10 atm $H_2$, 3.5 days) over 10% palladium on carbon in ethanol (50 mL). The resulting product 8 (as a solution in ethanol) was used directly with 2,4-pentanedione (0.3 mmol, 1.6 mL) and heated at reflux for 18 hours. The solvent was evaporated and the resulting residue taken up in dichloromethane (50 mL). The organic solution was washed with water (3×20 mL) and brine (20 mL) and dried over sodium sulphate. Evaporation of the dichloromethane gave a beige/yellow solid 9 (0.30 g, 0.84 mmol, 62%). $^1$H-NMR (CDCl$_3$) $\delta_H$: 1.79-1.84 (2H, m), 1.91 (6H, s), 2.10 (6H, s), 2.74-2.79 (2H, m), 3.56 (2H, s), 3.76 (2H, m), 4.82 (2H, m), 7.15-7.27 (5H, m). $^{13}$C-NMR $\delta_C$: 18.6, 30.2, 53.6, 62.1, 65.8, 68.0, 127.1, 128.5, 129.0, 142.0, 157.3, 204.2. m.p. 154-159° C.

Cyclohexane-Based Diamine Acen Ligand (14)

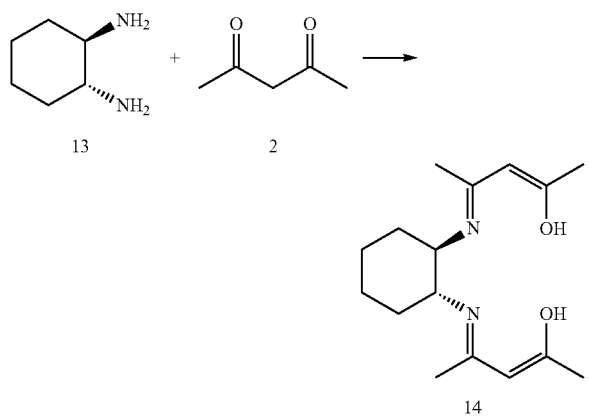

Compound 14 is disclosed in Pang, X., et al. *Journal of Organometallic Chemistry* 692 (2007) 5605-5613.

(R,R)-1,2-diaminocyclohexane dihydrochloride (13) (3.0 g, 16.0 mmol), and sodium methoxide (1.7 g, 32.0 mmol) were added to a 1:1 mixture of methanol and ethanol (50 mL) and heated to reflux with stirring for 20 minutes. Acetylacetone (2) (3.3 mL, 32.0 mmol) was then added and the reaction refluxed for 18 hours. The solvent was then evaporated in vacuo and the residue washed with diethyl ether (3×50 mL) to give the ligand as a pale yellow powder (3.6 g, 13.0 mmol, 81%).

Acen Methyl Ester Ligand (18)

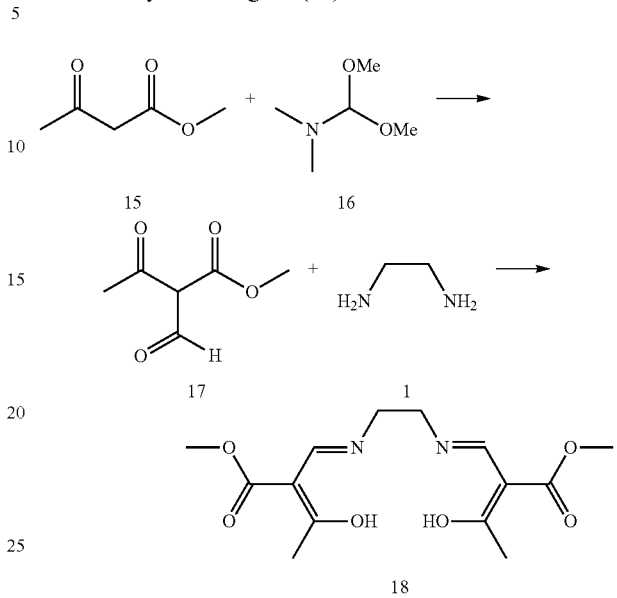

Compound 14 is disclosed in Mukaiyama, T. et al. *Chemistry Letters* 1993, 327-330. Methyl acetoacetate (15) (4.6 mL, 43.0 mmol) and dimethylformamide dimethylacetal (5.7 mL, 43.0 mmol) were stirred at ambient temperature for two hours during which time the reaction turned from colourless to orange. Then, a 2M aqueous solution of sodium hydroxide (50 mL) was added and the reaction stirred for a further two hours during which time the solution became yellow. The reaction was poured into a separating funnel and water (50 mL) and dichloromethane (50 mL) were added and the aqueous phase neutralized with 1M aqueous hydrochloric acid. The product was extracted using further washings of dichloromethane (5×50 mL), dried with sodium sulphate, filtered and evaporated in vacuo. The resulting bright yellow oil (17) (6.0 g) became red/orange on standing and was used directly in the next step without further purification.

The methyl 2-formyl 3-oxobutanoate (17) (6.0 g) was dissolved in ethanol (50 mL) and 1,2-diaminoethane (1) (1.4 mL, 21.5 mmol) was added. A yellow precipitate formed immediately and the reaction was allowed to stir for one hour at ambient temperature. The solvent was then evaporated in vacuo and the resulting material washed with diethyl ether (2×30 mL) to give the acen ligand (18) as a yellow powder (6.1 g, 20.0 mmol, 91%). Mp>160° C. (decomp.), $v_{max}$(ATR) 3400-2600 br, 3244 w, 2955 w, 1702 s and 1622 cm$^{-1}$ s; $^1$H NMR (CDCl$_3$): 11.06 (2H, br), 7.89 (1H, s), 7.85 (1H, s), 3.70 (6H, s), 3.5-3.6 (4H, m), 2.46 (6H, s).

Cyclohexane-Based Acen Methyl Ester Ligand (18)

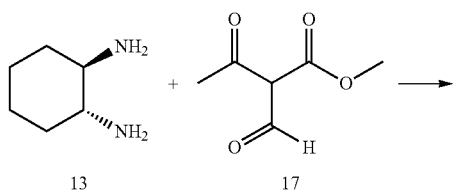

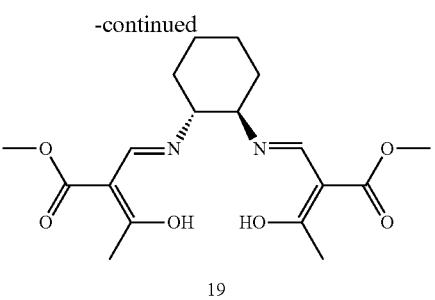

19

(R,R)-1,2-diaminocyclohexane dihydrochloride (13) (3.0 g, 16.0 mmol) and sodium methoxide (1.7 g, 32.0 mmol) were added to a 1:1 mixture of methanol and ethanol (50 mL) and heated to reflux with stirring for 20 minutes. Methyl 2-formyl 3-oxobutanoate (17) (4.6 g, 32.0 mmol) was dissolved in ethanol (40 mL) and added to the refluxing solution of diamine. The reaction was allowed to stir under reflux for 20 hours during which time the solution became yellow. The solvent was then evaporated in vacuo giving an orange gel which was rinsed with hexane (2×30 mL) to give the ligand as a yellow oil (5.1 g, 14.0 mmol, 87%). $[\alpha]_D^{23}$ -524 (c=0.1, MeCN); $\nu_{max}$(ATR) 3400-2400 br, 2943 m, 2864 m, 1696 m and 1632 cm$^{-1}$ s; $^1$H NMR (CDCl$_3$): 10.93 (2H, br), 8.31 (2H, br s), 3.61 (6H, s), 3.1-3.3 (2H, m), 2.42 (6H, s), 1.9-1.7 (4H, m), 1.4-1.2 (4H, m).

Example 1

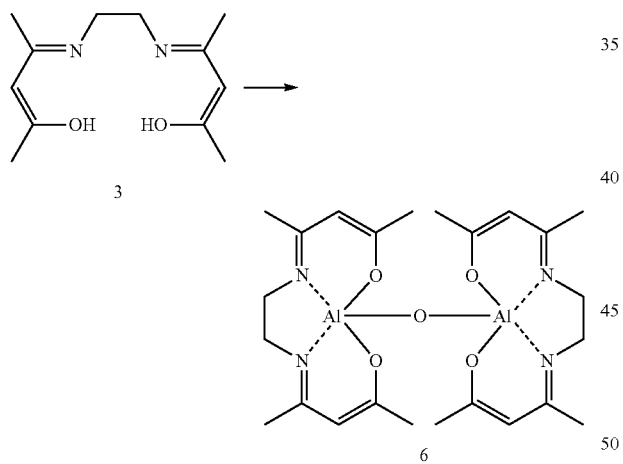

Acen ligand (3) (1.0 g, 4.5 mmol) was dissolved in toluene (25 mL) and heated to reflux under a nitrogen atmosphere. Aluminium triethoxide (1.5 g, 8.9 mmol) was then added and the reaction refluxed for 4 hours with stirring. The toluene was then removed by evaporation in vacuo and the resulting material taken up in dichloromethane (50 mL) and washed with water (3×20 mL). Evaporation of the organic layer gave a yellow powder to which was added diethyl ether (30 mL). The desired complex (6) (1.0 g, 2.0 mmol, 86%) was obtained as an off-white/light yellow crystalline solid by suction filtration.

mp: decomp >270° C.

$\nu_{max}$(ATR) 1605 (m), 1522 (s) and 1419 cm$^{-1}$ (m).

$\delta_H$(CDCl$_3$) 5.11 (4H, s), 3.7-3.4 (8H, m), 2.03 (12H, s), 1.99 (12H, s).

$\delta_C$(CDCl$_3$) 199.4, 177.4, 99.8, 46.2, 25.6, 21.7.

m/z (ES) 515.2 (MH$^+$), 281.1.

Found: 515.2358, C$_{24}$H$_{37}$N$_4$O$_5$Al$_2$ (MH$^+$) requires 515.2395.

Example 2

Salacen ligand (5) (1.0 g, 4.1 mmol) was dissolved in toluene (40 mL) and heated to reflux. Aluminium triethoxide (1.3 g, 8.3 mmol) was added and the reaction refluxed for four hours under a nitrogen atmosphere. The solution was allowed to stir and cool to room temperature overnight. The solvent was evaporated under vacuum and the resulting material taken up in dichloromethane (50 mL) and washed with water (3×20 mL). Diethyl ether (ca. 25 mL) was added to the resulting residue after evaporation of the solvent. The flask was cooled in ice and a yellow precipitate formed and was collected by filtration to give the desired complex (7) as a light yellow solid (0.95 g, 1.7 mmol, 84%).

mp: decomp >230° C.

$\nu_{max}$(ATR) 1637 (m), 1603 (m), 1526 (m), 1478 (m), 1455 (m) and 1408 cm$^{-1}$ (w).

m/z (ES) 559.2 (MH$^+$), 537.2, 581.2.

Found: 559.2083, C$_{28}$H$_{33}$N$_4$O$_5$Al$_2$ (MH$^+$) requires 559.2082.

Example 3

(i)

Bimetallic aluminium(acen) complex (6) (22 mg, 0.043 mmol) was weighed into a glass sample vial to which tetra-n-butyl ammonium bromide (TBAB) (13.5 mg, 0.042 mmol) was added. The vial was placed into a sealed flask containing a second vial filled with solid CO$_2$ pellets. The pressure of the system was regulated with a balloon. After saturation of the reaction vessel with $CO_2$ gas, styrene oxide (0.2 g, 1.7 mmol) was added via a syringe to the catalyst-TBAB mixture. The reaction was stirred at 30° C. for 24 hours. Samples were removed by a syringe and analysed by gas chromatography (or $^1$H NMR spectroscopy) after 3 hours (33% conversion of styrene oxide to styrene carbonate), 6 hours (52% conversion of styrene oxide to styrene carbonate) and 24 hours (85% conversion of styrene oxide to styrene carbonate). After this time was the reaction was worked up and an isolated yield of 81% was obtained.

Styrene carbonate: mp 54-56° C. $\delta_H$(CDCl$_3$) 7.4-7.3 (5H, m), 5.67 (1H, t J 8.0 Hz), 4.79 (1H, t J 8.3 Hz), 4.33 (1H, t J 8.0 Hz).

(ii) Using the same procedure with various epoxides, the following results were obtained with the aluminium(acen) complex (6) and aluminium(salacen) complex (7) and for comparison aluminium(salen) complex (C1) which was synthesised as follows:

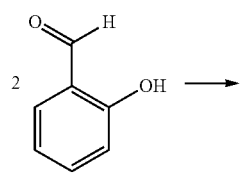

(a)

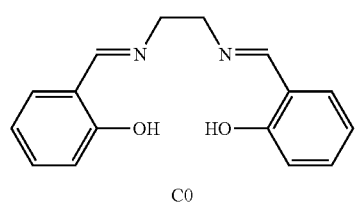

C0

Ethylenediamine (50 mmol, 3.3 mL) was added via a syringe to a stirred solution of salicylaldehyde (100 mmol, 10.5 mL) in ethanol (100 mL). A yellow precipitate formed immediately. The reaction mixture was refluxed for 3 hours and the solvent was then removed in vacuo to leave a yellow crystalline solid which was washed with diethyl ether (ca. 100 mL) to give salen ligand (C0) (12.0 g, 90%). Mp. 126-130° C. $^1$H NMR 3.96 (4H, s, CH$_2$CH$_2$), 6.87 (2H, t J=8.4 Hz, 2×H$_{Ar}$), 6.97 (2H, t J=8.7 Hz, 2×H$_{Ar}$), 7.2-7.3 (4H, m, 4×H$_{Ar}$), 8.38 (2H, s, 2×CH=N), 13.23 (2H, s, 2×OH).

(b)

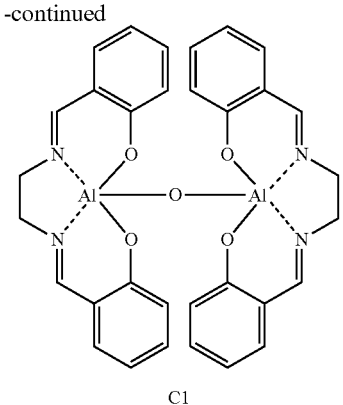

C1

Salen ligand (C0) (1.0 g, 3.9 mmol) and aluminium triethoxide (1.2 g, 7.4 mmol) were dissolved in dry toluene (25 mL). The reaction mixture was refluxed for 4 hours after which the toluene was evaporated and the resulting yellow residue taken up in dichloromethane and washed with water (3×100 mL) and saturated brine (100 mL). After evaporation of the organic phase, a light yellow powder was obtained which was washed with diethyl ether (ca. 50 mL) and dried to give salen complex (C1) (1.2 g, 49%). $^1$H NMR 3.87 (8H, s, 2×CH$_2$CH$_2$), 6.7-6.9 (8H, m, 8×H$_{Ar}$), 7.1-7.3 (8H, m, 8×H$_{Ar}$), 8.29 (4H, s, 4×CHN). $^{13}$C NMR 60.14, 65.09, 117.36, 119.00, 131.81, 132.74, 161.46, 166.85. m/z (ESI) Found: 603.1775 C$_{32}$H$_{25}$N$_4$O$_5$Al$_2$ (MH$^+$), Requires 603.1769.

|  |  | Conversion % | | |
|---|---|---|---|---|
| Catalyst | Substrate (R—) | 3 h | 6 h | 24 h |
| 6 | Ph— | 33 | 52 | 85 (81)[b] |
| 7 |  | 60 | 72 | 93 |
| C1 |  | 81 | 93 | 100 |
| 6 | CH$_3$(CH$_2$)$_3$— | 97 | 97 | 100 (94)[b] |
| 7 |  | 95 | 99 | 100 |
| 6 | CH$_3$(CH$_2$)$_7$— | 31 | 48 | 92 (89)[b] |
| 7 |  | 43 | 59 | 99 |
| 6 | HOCH$_2$— | 33 | 67 | 98 (90)[b] |
| 7 |  | 48 | 63 | 100 |
| 6 | ClCH$_2$— | 89 | 100 | 100 (91)[b] |
| 7 |  | 76 | 98 | 100 |
| 6[a] | CH$_3$— | 42 | 52 | 73 (70)[b] |
| 7[a] |  | 39 | 42 | 70 |
| 6[c] | H— |  |  | (58)[b] |
| 7[c] |  |  |  | (100)[b] |

[a] Reaction was carried out at 0° C.
[b] Isolated yield in brackets.
[c] Reactions were carried out in a stainless steel reactor with CO$_2$ under pressure (<3 bar).

GC Retention Times:
Styrene oxide (7.35 mins), styrene carbonate (12.08 mins)
Hexene oxide (3.56 mins), hexene carbonate (9.80 mins)
Decene oxide (8.98 mins), decene carbonate (13.40 mins)
Propylene carbonate (5.26 mins)
Ethylene carbonate (5.98 mins)
NMR Data for carbonates: $\delta_H$(CDCl$_3$):
1,2-Hexene carbonate: $\delta_H$(CDCl$_3$) 4.65 (1H, m) 4.49 (1H, t J 7.6 Hz), 4.01 (1H, t J 7.1 Hz), 1.7-1.6 (2H, m), 1.4-1.3 (4H, m), 0.89 (3H, t J 6.6 Hz).

1,2-Decene carbonate: $\delta_H$(CDCl$_3$) 4.7-4.6 (1H, m), 4.49 (1H, t J 8.1 Hz), 4.03 (1H, t J 7.5 Hz), 1.24 (14H, m), 0.85 (3H, t J 6.6 Hz).

Propylene carbonate: $\delta_H$(CDCl$_3$) 4.8-4.7 (1H, m), 4.55 (1H, t J 8.4 Hz), 4.02 (1H, dd J 8.4, 7.3 Hz), 1.46 (3H, d J 6.3 Hz).

Glycidol carbonate: 4.8-4.7 (1H, m), 4.5-4.4 (2H, m), 4.00 (1H, dd J 3.2, 12.9 Hz), 3.75 (1H, dd J 3.5, 12.7 Hz).

Epichlorohydrin carbonate: 5.0-4.9 (1H, m), 4.60 (1H, t J 8.7 Hz), 4.40 (1H, dd J 8.7, 5.7 Hz), 3.8-3.6 (2H, m).

Example 4

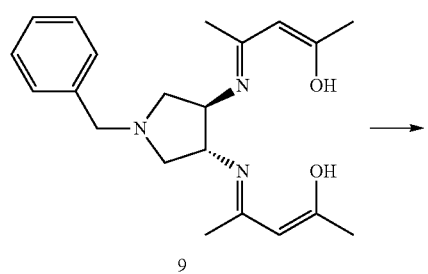

9

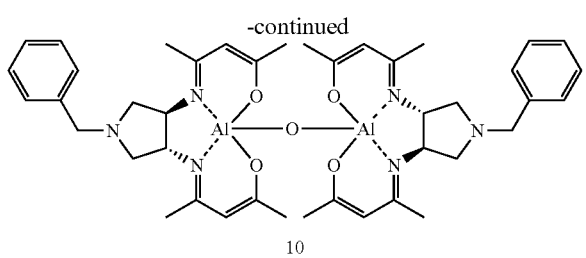

10

Ligand 9 (0.84 mmol, 0.30 g) was dissolved in dry toluene (60 mL) and heated to reflux. Aluminium triethoxide (1.68 mmol, 0.27 g) was added and heated for 24 hours. The resulting solution was washed with water (3×15 mL) and brine (15 mL) and dried over sodium sulphate. Evaporation yielded complex 10 as a yellow powder (0.32 mmol, 0.24 g, 75%). $^1$H-NMR (CDCl$_3$) $\delta_H$: 1.78-1.85 (4H, m), 2.08 (12H, s), 2.11 (12H, s), 2.73-2.79 (4H, m), 3.58 (4H, s), 3.78 (2H, m), 4.51 (2H, m), 7.15-7.26 (10H, m). $^{13}$C-NMR $\delta_C$: 19.6, 25.7, 62.1, 65.7, 67.6, 109.0, 127.1, 128.5, 129.0, 142.0, 155.8, 164.6. m.p. decomp >210° C. m/z (ES) 381.2 (MH$^+$), 412.2 (OCH$_3$H$^+$). HRMS (ESI): MH$^+$ (C$_{21}$H$_{28}$N$_3$O$_2$Al$^+$) 381.1997. found 381.2011.

Example 5

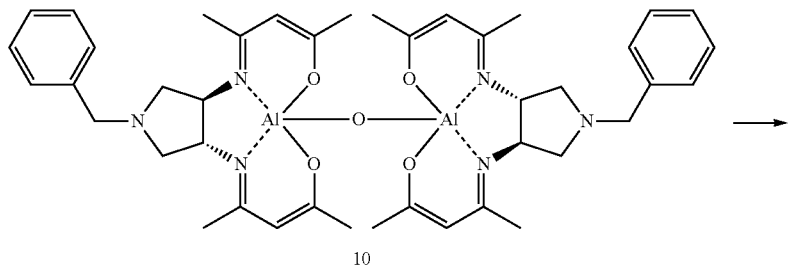

10

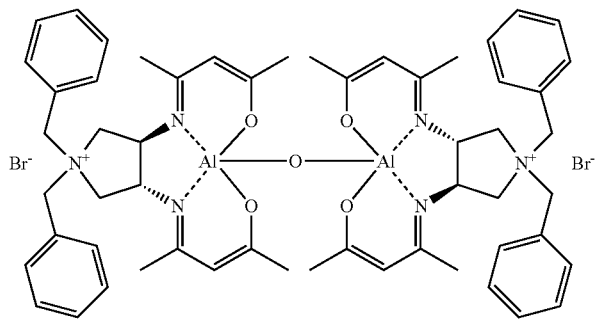

11

Complex 10 (0.13 mmol, 0.1 g) was dissolved in acetonitrile (5 mL) and benzyl bromide was added (6 eq., 0.8 mmol, 0.1 mL). The resulting mixture was heated to reflux and stirred for 24 hours during which time a dark orange precipitate formed. After cooling, the solvent was evaporated and the resulting material taken up in ether (ca. 20 mL) and filtered yielding 11 as a yellow/orange solid.

Example 6

(i) Complex 10 was used as a catalyst in the method of Example 3(i), and had a yield of 6% at 24 hours.

(ii) Complex 11 was used as a catalyst in the method of Example 3(i), except for the absence of the TBAB cocatalyst. The yield was 5% after 24 hours.

Example 7

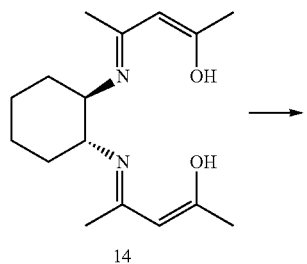

14

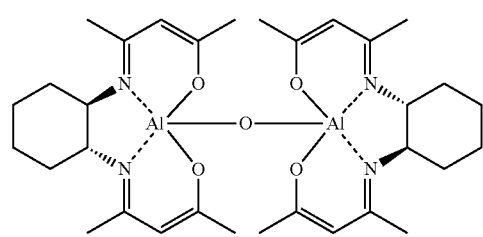

20

(R,R)-Cyclohexanediamine acen ligand (14) (3.0 g, 11.0 mmol) was added to a 5:1 dry toluene/acetonitrile solution (60 mL). Aluminium triethoxide (2.1 g, 13.0 mmol) was then added and the reaction refluxed for 20 hours. The solvent was evaporated in vacuo and the residue taken up in dichloromethane (80 mL). The resulting slurry was washed with water (3×50 mL) and saturated brine (50 mL). The organic phase was then dried over sodium sulphate, filtered and evaporated in vacuo. The residue was rinsed with diethyl ether (ca. 30 mL) and dried in vacuo for an hour to give the aluminium complex (20) as a pale yellow powder (0.54 g, 0.86 mmol, 16%). Mp>170° C. (decomp.), $[\alpha]_D^{23}$-688 (c=0.1, MeCN), $v_{max}$(ATR) 2931 w, 2859 w, 1606 s and 1577 cm$^{-1}$ s; $^1$H NMR (CDCl$_3$): 4.89 (2H, s), 3.1-3.2 (2H, m), 1.98 (6H, s), 1.83 (6H, s), 2.0-1.7 (4H, m), 1.5-1.2 (4H, m).

Example 8

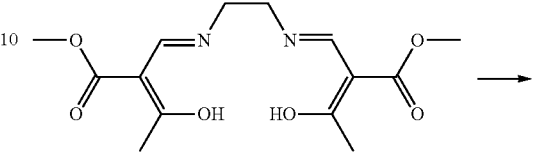

18

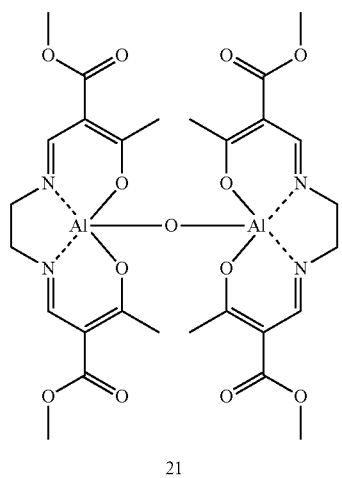

21

Acen methyl ester ligand (18) (3.0 g, 10.0 mmol) was added to dry toluene and the mixture was heated to reflux to dissolve the ligand. Aluminium triethoxide (1.9 g, 12.0 mmol) was added and the reaction refluxed for 20 hours. The solvent was removed in vacuo, taken up in dichloromethane (50 mL) and washed with water (3×20 mL) and brine (20 mL). The organic phase was dried over sodium sulphate and evaporated in vacuo. The residue was dried in vacuo to give the aluminium complex (21) as a pale yellow powder (3.2 g, 4.6 mmol, 92%). Mp 188-190° C., $v_{max}$(ATR) 2949 w, 1695 m and 1616 cm$^{-1}$ s; $^1$H NMR (CDCl$_3$): 8.31 (1H, s), 8.09 (1H, s), 3.73 (4H, br, s), 3.69 (6H, s), 2.40 (6H, s); m/z (ESI, MeOH) 705 (M+Me)$^+$, 691 MH$^+$.

Example 9

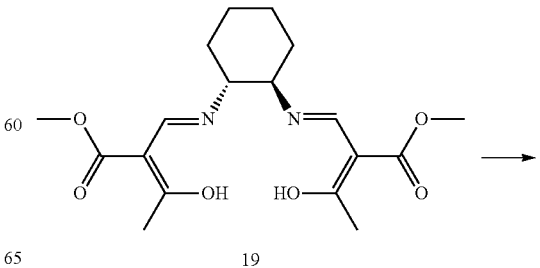

19

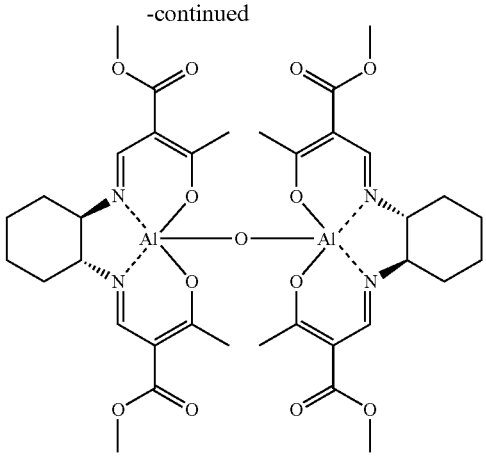

22

(R,R)-Cyclohexanediamine acen methyl ester (19) (3.0 g, 8.2 mmol) was added to dry toluene and the mixture was heated to reflux to dissolve the ligand. Aluminium triethoxide (2.7 g, 16.0 mmol) was added and the reaction refluxed for 22 hours. The solvent was removed in vacuo and the residue taken up in dichloromethane (50 mL) and washed with water (3×20 mL) and brine (20 mL). The organic phase was dried over sodium sulphate and evaporated in vacuo. The residue was dried in vacuo to give the aluminium complex (22) as a pale yellow powder (2.9 g, 3.6 mmol, 89%). $[\alpha]_D^{23}$-488 (c=0.1, MeCN), $^1$H NMR (CDCl$_3$): 8.4-7.8 (4H, m), 3.5-3.4 (16H, m), 2.24 (12H, s), 1.9-1.4 (8H, m), 1.2-0.8 (8H, m).

Example 10

Complexes 20, 21 and 22 were used as a catalyst in the method of Example 3(i), and had yields as shown in the table below:

| Catalyst | Conversion % | | |
|---|---|---|---|
| | 3 h | 6 h | 24 h |
| 20 | 2 | 6 | 16 |
| 21 | 7 | 15 | 36 |
| 22 | 3 | 6 | 15 |

The invention claimed is:
1. A dimeric aluminium catalyst of formula I:

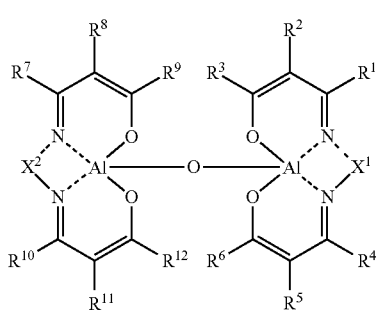

(I)

wherein:
a) each of the substituents $R^1$, $R^2$, $R^3$, $R^4$, $R^5$, $R^6$, $R^7$, $R^8$, $R^9$, $R^{10}$, $R^{11}$ and $R^{12}$, is independently selected from H, halo, optionally substituted $C_{1-20}$ alkyl, optionally substituted $C_{5-20}$ aryl, optionally substituted $C_{3-20}$ heterocyclyl, ether and nitro, where $R^2$, $R^5$, $R^8$ and $R^{11}$ may additionally be independently selected from optionally substituted ester or optionally substituted acyl or the pairs of $R^2$ and $R^3$, $R^5$ and $R^6$, $R^8$ and $R^9$ and $R^{11}$ and $R^{12}$ may independently together form a $C_{2-4}$ alkylene chain, optionally substituted by one or more groups selected from $C_{1-4}$ alkyl and $C_{5-7}$ aryl; or
b) $R^5$ and $R^6$ together with the carbon atoms to which they are attached form an optionally substituted benzene ring of formula:

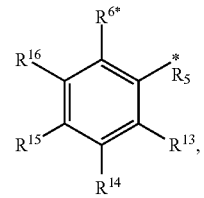

and
$R^{11}$ and $R^{12}$ together with the carbon atoms to which they are attached form an optionally substituted benzene ring of formula:

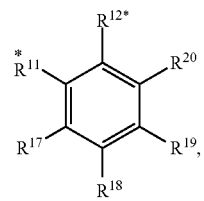

each of the substituents $R^1$, $R^2$, $R^3$, $R^4$, $R^7$, $R^8$, $R^9$, $R^{10}$, $R^{13}$, $R^{14}$, $R^{15}$, $R^{16}$, $R^{17}$, $R^{18}$, $R^{19}$ and $R^{20}$, is independently selected from H, halo, optionally substituted $C_{1-20}$ alkyl (including CAr$_3$, where Ar is a $C_{5-20}$ aryl group), optionally substituted $C_{5-20}$ aryl, optionally substituted $C_{3-20}$ heterocyclyl, ether and nitro;
$X^1$ and $X^2$ are independently either (i) a $C_{2-5}$ alkylene chain, which is optionally substituted by one or more groups selected from $C_{1-4}$ alkyl and $C_{5-7}$ aryl, or a $C_{1-3}$ bisoxyalkylene chain, which is optionally substituted by one or more groups selected from $C_{1-4}$ alkyl and $C_{5-7}$ aryl or (ii) represent a divalent group selected from $C_{5-7}$ arylene, $C_{9-10}$ arylene, bi-$C_{5-7}$ aryl, bi-$C_{9-10}$ aryl, $C_{5-7}$ cyclic alkylene and $C_{3-7}$ heterocyclylene, which may be optionally substituted, wherein:
(i) (a) at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ (where present) is selected from L-A, where L is a single bond or a $C_{1-10}$ alkylene group and A is an onium group paired with a counterion selected from Cl, Br and I; and/or
(b) at least one of $X^1$ and $X^2$ is a divalent $C_{3-7}$ heterocyclene group, containing a ring atom which is a quaternary nitrogen forming part of an ammonium group paired with a counterion selected from Cl, Br and I; and/or (c) at least one of $X^1$ and $X^2$ is a $C_{2-5}$ alkylene chain or a $C_{1-3}$ bisoxyalkylene chain, substituted by a group -Q-L-A, where Q is either —C(=O)—O—, —C(=O)—NH—, or a single bond; and/or (d) at least one of $R^2$, $R^5$, $R^8$ and $R^{11}$ is -Q'-L-A, where Q' is either —C(=O)—O— or —C(=O)—;

and/or (ii) (a) one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ (where present) is L-A', where L is as defined above and A' is an onium linking group bound to a solid support and paired with a counterion selected from Cl, Br and I; or (b) one of $X^1$ and $X^2$ is a divalent $C_{3-7}$ heterocyclene group, containing a ring atom which is a quaternary nitrogen forming part of an ammonium linking group bound to a solid support and paired with a counterion selected from Cl, Br and I; or (c) one of $X^1$ and $X^2$ is a $C_{2-5}$ alkylene chain or a $C_{1-3}$ bisoxyalkylene chain, substituted by a group -Q-L-A'; or (d) one of $R^2$, $R^5$, $R^8$ and $R^{11}$ is -Q'-L-A'.

2. A catalyst according to claim 1, wherein $X^1$ and $X^2$ are independently selected from an unsubstituted $C_{2-5}$ alkylene chain and an unsubstituted $C_{1-3}$ bisoxylakylene chain.

3. A catalyst according to claim 1, wherein $X^1$ and $X^2$ are the same.

4. A catalyst according to claim 1, wherein those of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ (where present) which do not comprise -L-A or -L-A' are independently selected (where appropriate) from H, $C_{1-7}$ alkyl, ether and nitro.

5. A catalyst according to claim 1, wherein: (a) $R^1=R^4=R^7=R^{10}=H$; and/or (b) $R^3=R^6=R^9=R^{12}=H$; and/or (c) $R^5$ and $R^6$, and $R^{11}$ and $R^{12}$ do not form fused benzene rings.

6. A catalyst according to claim 1, wherein L is an unsubstituted $C_{1-3}$ alkylene group.

7. A catalyst according to claim 1, wherein one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ (where present) is selected from L-A' and A' is selected from —NH(CH$_3$)(CH$_2$)—, —NH(CH(CH$_3$)$_2$)(C(CH$_3$)$_2$)—, —N(CH$_3$)$_2$(CH$_2$)—, —N(CH$_2$CH$_3$)$_2$(CH$_2$CH$_2$)—, and —NHPh(CH$_2$)—.

8. A catalyst according to claim 1, wherein: (a) $X^1$ or $X^2$ is substituted by -Q-L-A' and is of formula:

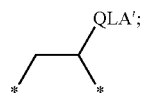

or (b) $X^1$ or $X^2$ is a divalent $C_{3-7}$ heterocyclene group containing a ring atom which is a quaternary nitrogen forming part of an ammonium linking group, and is of formula:

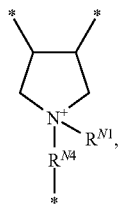

where $R^{N1}$ is selected from H, $C_{1-7}$ alkyl and $C_{5-20}$ aryl and where $R^{N4}$ is a $C_{1-7}$ alkylene group.

9. A catalyst according to claim 1, wherein the ammonium counter group is Br$^-$.

10. A process for the production of cyclic carbonates comprising contacting an epoxide with carbon dioxide in the presence of a catalyst according to claim 1.

11. The process of claim 10, wherein the catalysed reaction is:

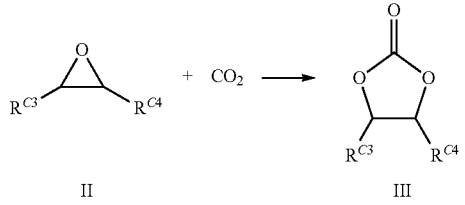

wherein $R^{C3}$ and $R^{C4}$ are independently selected from H, optionally substituted C1-10 alkyl, optionally substituted C3-20 heterocyclyl and optionally substituted C5-20 aryl, or $R^{C3}$ and $R^{C4}$ form an optionally substituted linking group between the two carbon atoms to which they are respectively attached.

* * * * *

UNITED STATES PATENT AND TRADEMARK OFFICE
CERTIFICATE OF CORRECTION

PATENT NO. : 9,006,425 B2  
APPLICATION NO. : 13/254143  
DATED : April 14, 2015  
INVENTOR(S) : Michael North Page 1 of 1

It is certified that error appears in the above-identified patent and that said Letters Patent is hereby corrected as shown below:

In the Specification

Column 13, Line 33, replace "amido" with --amino--

Signed and Sealed this  
Twenty-ninth Day of September, 2015

Michelle K. Lee  
*Director of the United States Patent and Trademark Office*